(12) United States Patent
Raucher et al.

(10) Patent No.: US 8,252,740 B2
(45) Date of Patent: Aug. 28, 2012

(54) THERMALLY-TARGETED DELIVERY OF MEDICAMENTS INCLUDING DOXORUBICIN

(75) Inventors: Drazen Raucher, Madison, MS (US); Gene Bidwell, III, Jackson, MS (US); Waldemar Priebe, Houston, TX (US); Izabela Fokt, Houston, TX (US)

(73) Assignee: The University of Mississippi Medical Center, Jackson, MS (US)

( * ) Notice: Subject to any disclaimer, the term of this patent is extended or adjusted under 35 U.S.C. 154(b) by 717 days.

(21) Appl. No.: 12/162,283

(22) PCT Filed: Jan. 29, 2007

(86) PCT No.: PCT/US2007/061240
§ 371 (c)(1),
(2), (4) Date: Jun. 24, 2009

(87) PCT Pub. No.: WO2007/090094
PCT Pub. Date: Aug. 9, 2007

(65) Prior Publication Data
US 2010/0022466 A1    Jan. 28, 2010

Related U.S. Application Data

(60) Provisional application No. 60/762,919, filed on Jan. 27, 2006.

(51) Int. Cl.
*A61K 38/02* (2006.01)
*C07K 7/06* (2006.01)
*C07K 14/00* (2006.01)

(52) U.S. Cl. ........ 514/1.2; 514/1.3; 514/19.3; 514/19.4; 530/300; 530/345

(58) Field of Classification Search .................. None
See application file for complete search history.

(56) References Cited

U.S. PATENT DOCUMENTS
6,214,345 B1 * 4/2001 Firestone et al. .......... 424/178.1
2003/0124742 A1   7/2003 Prakash
2004/0234497 A1  11/2004 Luo et al.

FOREIGN PATENT DOCUMENTS
WO   WO2006/001806   1/2006

OTHER PUBLICATIONS

Dreher, M.R. et al., Evaluation of an elastin-like polypeptide-doxorubincin conjugate for cancer therapy; Journal of Controlled Release; 2003; vol. 91; pp. 31-43.

(Continued)

*Primary Examiner* — Jeffrey E Russel
(74) *Attorney, Agent, or Firm* — Stites & Harbison PLLC; Mandy Wilson Decker; Richard S Myers, Jr.

(57) ABSTRACT

Elastin-like polypeptide (ELP) serves as a vector for thermally-targeted delivery of therapeutics, including cytotoxic chemotherapeutic drugs such as doxorubicin. Examples of an ELP-based delivery vehicle can comprise: (1) a cell penetrating peptide, such as a Tat peptide, (2) ELP, and (3) the lysosomally degradable glycylphenylalanylleucylglycine (GFLG) (SEQ ID NO: 3) spacer and a cysteine residue (SEQ ID NO: 4) conjugated to therapeutic such as doxorubicin, or an analog thereof.

14 Claims, 11 Drawing Sheets

OTHER PUBLICATIONS

Massodi, I, et al., Evalution of cell penetrating peptides fused to elastin-like polypeptide for drug delivery; Journal of controlled Release; 2005; vol. 108; pp. 396-408.

Meyer, D.E., et al., Targeting a Genetically Engineered Elastin-like Polypeptide to Solid Tumors by Local Hyperthemia; Cancer Research; Feb. 15, 2001; vol. 61, pp. 1548-1554.

Massodi, I, et al., Inhibition of ovarian cancer cell metastasis by a fusion polypeptide Tat-ELP; Clin Exp Metastasis; 2009; 26; pp. 251-260.

Bidwell, G.L., et al Targeting a c-Myc inhibitory polypeptide to specific intracellular compartments using cell penetrating peptides; Journal of Controlled Relase; 2009, (article in press).

Massodi, I., et al A thermally responsive Tat-elastin-like polypeptide fusion protein induces membrane leakage, apoptosis, and cell death in human breast cancer cells; Journal of Drug Targeting; Nov. 2007; 15(9); pp. 611-622.

Bidwell GL, III, et al Application of thermally responsive polypeptides directed against c-Myc transcriptional function for cancer therapy; Mol Cancer Ther 2005; 4(7): 1076-85.

Bidwell GL, III, et al Enhancing the antiproliferative effect of topoisomerase II inhibitors using a polypeptide inhibitor of c-Myc; Biochemical Pharmacology; 2006; 71; pp. 248-256.

Bidwell GL, III, et al Development of elastin-like polypeptide for thermally targeted delivery of doxorubicin; Biochemical Pharmacology; 2007; 73; pp. 620-631.

Bidwell GL, III, et al A thermally targeted elastin-like polypeptide-doxorubicin conjugate overcomes drug resistance; Invest New Drugs; 2007; 25; pp. 313-326.

Raucher, et al Thermally targeted delivery of chemotherapeutics and anti-cancer peptides by elastin-like polypeptide; Expert Opinion, Drug Deliv. (2008) 5(3):1-16.

* cited by examiner

```
                             SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Elastin-like polypeptide
<220> FEATURE:
<221> NAME/KEY: X
<222> LOCATION: (1)..(1)
<223> OTHER INFORMATION: X is equal to any amino acid except proline

<400> SEQUENCE: 1

Xaa Gly Val Pro Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Elastin-like polypeptide variant
<220> FEATURE:
<221> NAME/KEY: X
<222> LOCATION: (4)..(4)
<223> OTHER INFORMATION: X is equal to Valine, Glycine, or Alanine

<400> SEQUENCE: 2
```

```
Val Pro Gly Xaa Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Cleavable peptide linker

<400> SEQUENCE: 3

Gly Phe Leu Gly
1

<210> SEQ ID NO 4
<211> LENGTH: 5
<212> TYPE: PRT
<213> ORGANISM: Artificial Sequence
<220> FEATURE:
<223> OTHER INFORMATION: Cleavable peptide linker with C-terminal
      cysteine

<400> SEQUENCE: 4

Gly Phe Leu Gly Cys
1               5

<210> SEQ ID NO 5
<211> LENGTH: 17
<212> TYPE: PRT
<213> ORGANISM: Drosophila melanogaster

<400> SEQUENCE: 5

Met Arg Gln Ile Lys Ile Trp Phe Gln Asn Arg Arg Met Lys Trp Lys
1               5                   10                  15

Lys

<210> SEQ ID NO 6
<211> LENGTH: 12
<212> TYPE: PRT
<213> ORGANISM: Human immunodeficiency virus

<400> SEQUENCE: 6

Met Tyr Gly Arg Lys Lys Arg Arg Gln Arg Arg Arg
1               5                   10

<210> SEQ ID NO 7
<211> LENGTH: 17
<212> TYPE: PRT
<213> ORGANISM: Artificial Sequence
<220> FEATURE:
<223> OTHER INFORMATION: MTS  - membrane translocating sequence

<400> SEQUENCE: 7

Met Ala Ala Val Ala Leu Leu Pro Ala Val Leu Leu Ala Leu Leu Ala
1               5                   10                  15

Pro

<210> SEQ ID NO 8
<211> LENGTH: 25
<212> TYPE: PRT
<213> ORGANISM: Bos taurus

<400> SEQUENCE: 8

Met Arg Arg Ile Arg Pro Arg Pro Pro Arg Leu Pro Arg Pro Arg Pro
1               5                   10                  15
```

```
Arg Pro Leu Pro Phe Pro Arg Pro Gly
            20                  25

<210> SEQ ID NO 9
<211> LENGTH: 28
<212> TYPE: PRT
<213> ORGANISM: Artificial Sequence
<220> FEATURE:
<223> OTHER INFORMATION: Trans - membrane transolcating sequence

<400> SEQUENCE: 9

Met Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu
            20                  25

<210> SEQ ID NO 10
<211> LENGTH: 19
<212> TYPE: PRT
<213> ORGANISM: Mus musculus

<400> SEQUENCE: 10

Met Leu Leu Ile Ile Leu Arg Arg Arg Ile Arg Lys Gln Ala His Ala
1               5                   10                  15

His Ser Lys

<210> SEQ ID NO 11
<211> LENGTH: 5
<212> TYPE: PRT
<213> ORGANISM: Artificial Sequence
<220> FEATURE:
<223> OTHER INFORMATION: oligopeptide

<400> SEQUENCE: 11

Gly Gly Pro Gly Gly
1               5

<210> SEQ ID NO 12
<211> LENGTH: 4
<212> TYPE: PRT
<213> ORGANISM: Artificial Sequence
<220> FEATURE:
<223> OTHER INFORMATION: oligopeptide

<400> SEQUENCE: 12

Trp Pro Gly Ser
1
```

THERMALLY-TARGETED DELIVERY OF MEDICAMENTS INCLUDING DOXORUBICIN

RELATED APPLICATION

This application claims priority from U.S. Provisional Application Ser. No. 60/762,919, filed Jan. 27, 2006.

FIELD OF THE INVENTION

The present invention generally relates to the field of targeted delivery systems for delivering therapeutic agents to tumors, in particular to tumor cells and tumor-associated cells. The invention further relates to methods of delivering a therapeutic agent to tumor cells and tumor-associated cells for the prevention and treatment of cancer by killing tumor cells and tumor-associated cells. Specifically, the delivery systems of the present invention are capable of delivering an increased amount of therapeutics to tumor cells and tumor-associated cells as compared to other delivery systems. In particular, the delivery systems of the present invention are capable of accumulating a higher amount of therapeutic agent in tumor cells, or in cells that contribute to tumor cell viability (e.g. vascular endothelial cells), and of leading to exposure of these cells to therapeutic levels of the agent for a longer period of time as compared to other delivery systems. The present invention also describes pharmaceutical compositions and tumor cells comprising the delivery systems of the present invention. The delivery systems and pharmaceutical compositions can be administered to a subject, preferably a human, alone or in combination, sequentially or simultaneously, with other prophylactic or therapeutic agents and/or anti-cancer treatments.

BACKGROUND OF THE INVENTION

Most chemotherapeutic drugs act on both normal as well as cancerous tissues. As such, one of the challenges in treating cancerous tumors with chemotherapy is maximizing the killing of cancer cells while minimizing the harming of healthy tissue. Depending on the administration route (e.g., intravenous) and nature of the drug (e.g., its physical and pharmacokinetic properties), oftentimes only a small fraction of the dose reaches the target cells; the remaining amount of drug acts on other tissues or is rapidly eliminated. Thus, the efficacy of traditional cytotoxic chemotherapy drugs is limited by their adverse effects on non-cancerous tissue. Only a small fraction of the administered dose of drug reaches the tumor site, while the rest of the drug is distributed throughout the body. This causes undesirable damage to normal tissue when used in doses required to eradicate cancer cells, resulting in a limited therapeutic index. Use of the topoisomerase II poison doxorubicin (Dox) is limited by the induction of myelosuppression and cardiotoxicity. Site-specific drug delivery vehicles would make chemotherapy more effective and less toxic by increasing the amount of drug reaching the intended target.

A commonly used approach to address the issue of drug delivery to solid tumors is to attach the drug to a macromolecular carrier. Soluble polymeric carriers are attractive for systemic drug delivery because polymer-drug conjugates preferentially accumulate in tumors due to their enhanced microvascular permeability and retention and exhibit significantly lower systemic toxicity compared to free drug. Studies have shown that water soluble polymer carriers can overcome multidrug resistance. The most compelling evidence for the advantages of using polymer-drug conjugates over free chemotherapeutic agents for the treatment of cancer comes from extensive preclinical and clinical studies by Kopecek and colleagues on the use of N-(2-hydroxypropyl)methacrylamide (HPMA) copolymers as drug carriers.

Elastin-like polypeptide (ELP) is a protein comprised of a five amino acid repeat (XGVPG, where X is any amino acid except proline (SEQ ID NO: 1)). ELPs are attractive as polymeric carriers for drug delivery because they undergo an inverse temperature phase transition. Below a characteristic transition temperature ($T_t$), ELPs are structurally disordered and highly solvated. But, when the temperature is raised above their $T_t$, they undergo a sharp (2-3° C. range) phase transition, leading to desolvation and aggregation of the biopolymer. This process is fully reversible when the temperature is lowered below $T_t$.

The phase transition of these polypeptides may be exploited for use in drug delivery by applying focused, mild hyperthermia to the tumor site. Systemically injected ELP will remain soluble and freely circulate at normal body temperature. However, at localized sites where hyperthermia is applied to raise the tissue above the ELP's $T_t$, the polypeptide will aggregate and accumulate. Attachment of drugs to ELP offers the capability to specifically deliver these drugs to the desired tissue by focused application of externally applied hyperthermia. The use of hyperthermia has an added advantage of increasing vessel permeability. The ELP-based drug delivery system described here combines the advantages of macromolecular delivery, hyperthermia, and thermal targeting.

A previous study demonstrated the ability of ELP to deliver doxorubicin into the cell cytoplasm and induce cytotoxicity, but with no significant enhancement in cell toxicity in response to heat. Since the ultimate goal of drug delivery by ELP is to thermally target the chemotherapeutic, it is imperative that cytotoxicity be enhanced in response to temperature increase. The present inventors have discovered a thermally responsive drug carrier, generated by modifying the sequence of ELP to include additional targeting features, and the result was a drug delivery vector that achieved a 20 fold enhancement of cell killing in response to hyperthermia.

SUMMARY OF THE INVENTION

An aspect of the present invention is a drug delivery compound and/or composition that targets a tumor site by applying local hyperthermia.

Another aspect of the present invention is a drug delivery compound that is soluble under physiological conditions ($T<T_t$), and it is cleared from circulation under these conditions. However, it will aggregate at sites where heat is applied ($T>T_t$), which will allow preferential accumulation of the drug only at the targeted, locally heated diseased sites.

Another aspect of the present invention is a drug delivery compound or composition for the selective delivery of a therapeutic/anticancer agent such as, for example, doxorubicin (DOX). The chemotherapeutic drug doxorubicin (Dox) is widely used as an antitumor agent in hematological malignancies and solid tumors. However, one of the limitations of its clinical use is that systemic administration of an effective dose of Dox results in nonselective cardiac toxicity and myelosuppression.

Another aspect of the preset invention is a thermally responsive polypeptide carrier for an anticancer agent such as, for example, the drug doxorubicin, which has the potential to be targeted to the tumor site by applying local hyperthermia. The thermally responsive polypeptide can be based on elastin-like polypeptide (ELP), such as a 59 kilodalton protein composed of repeated units of the amino acid sequence VPGXG (SEQ ID NO: 2). At a characteristic temperature called the transition temperature ($T_t$), ELP reversibly forms insoluble aggregates. This property may be exploited for thermally targeted delivery of ELP conjugated drugs.

In one embodiment, the delivery vehicle may comprise: (1) a cell penetrating peptide sequence (Tat peptide from HIV1), (2) ELP, an elastin-like polypeptide with $T_t$=about 40-42° C. and (3) a GFLG (SEQ ID NO: 3) peptide linker with a C-terminal cysteine (SEQ ID NO: 4) coupled to an anticancer agent such as, for example, the drug doxorubicin.

The protein transduction domain from the HIV Tat protein has been used to efficiently deliver proteins and therapeutic compounds across the cell membrane and the blood brain barrier (BBB). Therefore, it will mediate transport of the carrier-polypeptide across the cell membrane. Following cellular uptake, the proteolytically cleavable GFLG (SEQ ID NO: 3) peptide linker will be cleaved by lysosomal enzymes, allowing intracellular agent release and transport to the appropriate molecular site of action within the target cells.

Thus, as stated above, the present invention provides methods of delivering an increased amount of therapeutic/anticancer agent to tumors. In specific embodiments, the increase in exposure level of the tumor to the therapeutic agent is about 0.5-40 folds, and all values in-between, higher over a period of time as compared to that of using other delivery systems. In specific embodiments, the tumor is exposed to increased levels of agent by over about 2-99%, and all values in-between over a period of time as compared to that of using other delivery systems.

In other specific embodiments, the methods of the present invention further comprises administration of other therapies or therapeutic agents simultaneously or sequentially. That is, the invention further relates to combination therapies for treating cancer in a subject by administering to said subject a therapeutically or prophylactically effective amount of one or more delivery systems and/or pharmaceutical compositions, sequentially or simultaneously, with surgery, standard and experimental chemotherapies, hormonal therapies, biological therapies, immunotherapies, radiation therapies, embolization, and/or chemoembolization therapies for the treatment or prevention of cancer.

An example of a thermally responsive ELP polypeptide is modified with the addition of a cell penetrating peptide derived from the HIV-1 Tat protein (Tat) and by employing a cleavable tetrapeptide linker for attachment of the drug to the macromolecule. The Tat peptide is known to facilitate transport of large molecules across the plasma membrane, and a previous study demonstrated its ability to enhance ELP uptake by an endocytic mechanism. In addition, the ELP contains a tetrapeptide glycylphenylalanyIleucylglycyl (GFLG) linker (SEQ ID NO: 3) and a C-terminal cysteine residue (SEQ ID NO: 4). The thiol of the terminal cysteine is used for attachment of drugs, and the GFLG (SEQ ID NO: 3) linker can be cleaved by lysosomal proteases of the cathepsin family, resulting in intracellular drug release. In embodiments of the present invention, a thiol reactive derivative of doxorubicin (WP936) containing a maleimido moiety linked to the C-3' amino group was designed and synthesized. WP936 was attached to the C-terminal cysteine residue of the ELP carrier (Tat-ELP-GFLG-Dox (SEQ ID NO: 3)). The Dox delivery construct exhibited a $T_t$ of 40° C., and its cellular uptake was enhanced by both the Tat peptide and hyperthermia. Dox delivered by the ELP vector accumulated in the cell cytoplasm. The ELP-delivered Dox was cytotoxic to MES-SA uterine sarcoma cells, and the toxicity was enhanced 20 fold by the application of hyperthermia. The ELP-delivered Dox induced apoptosis by caspase activation in a temperature dependent manner.

BRIEF DESCRIPTION OF THE DRAWINGS

The following figures show embodiments of the present invention, and should not be construed to be limiting thereof.

DESCRIPTION OF THE INVENTION

Figure 1:
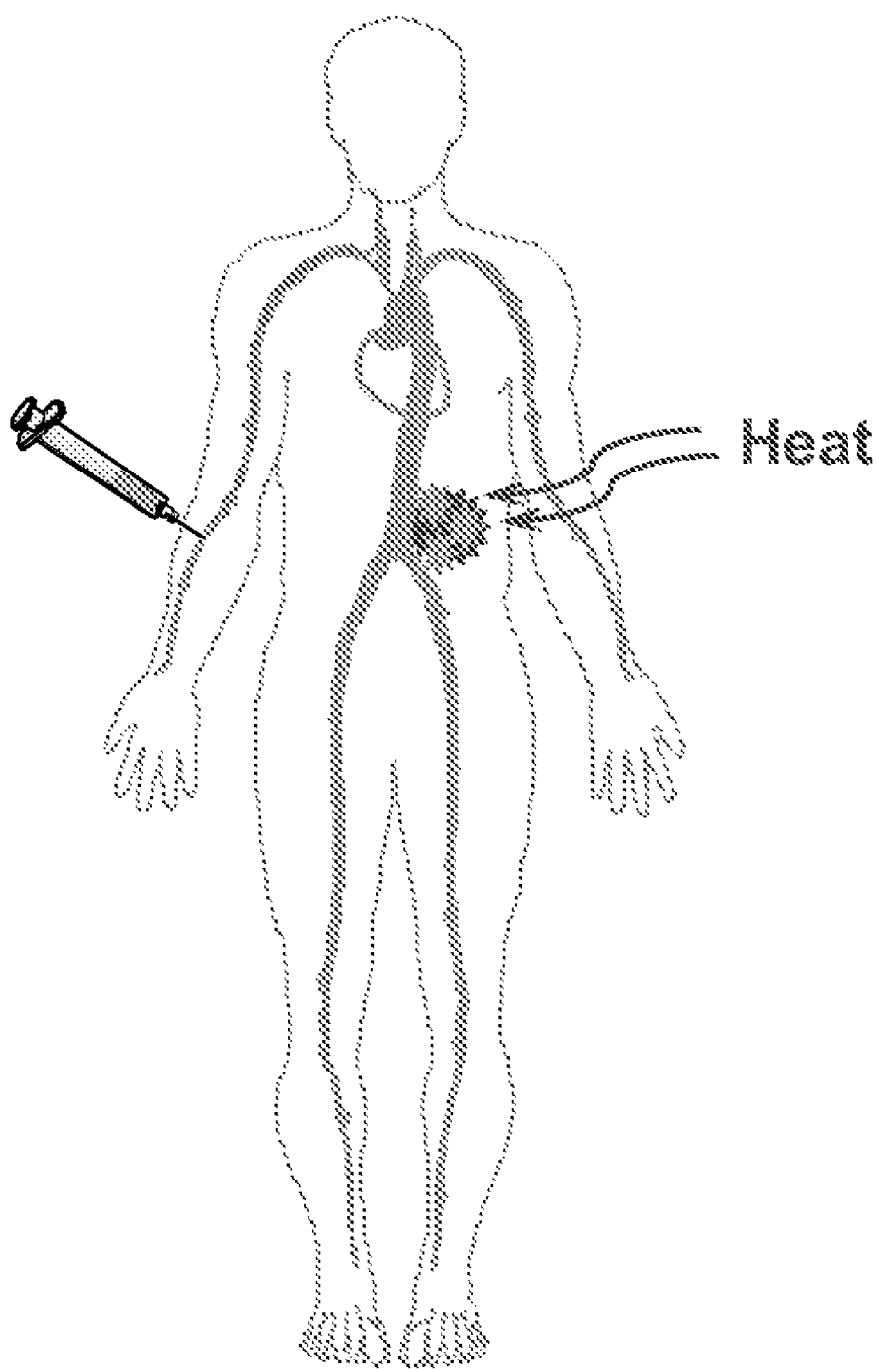
FIG. 1 shows an embodiment of the present invention. More specifically, this figure shows embodiments where intravenously delivered ELP polymers carrying DOX are likely to have low blood concentration and they will be rapidly cleared under physiological conditions ($T<T_t$). However they will aggregate at heated sites where $T>T_t$, allowing preferential accumulation of doxorubicin delivered by ELP.

One embodiment of the present invention is a drug delivery molecule which has the potential to be targeted to the applicable site by applying local hyperthermia. This drug-delivery polypeptide is soluble under physiological conditions ($T<T_t$), and it is likely to be cleared from circulation under these conditions. However, it will aggregate at sites where heat is applied ($T>T_t$), which will allow preferential accumulation of a drug (e.g., doxorubicin) only at the targeted, locally heated diseased sites (FIG. 1).

As indicated above, a major challenge in cancer chemotherapy is the selective delivery of small molecule anti-cancer agents to tumor cells. Water-soluble polymer-drug conjugates exhibit good water solubility, increased half-life, and potent anti tumor effects. By localizing the drug at the desired site of action, macromolecular therapeutics have improved efficacy and enhanced safety at lower doses. Since small molecule drugs and macromolecular drugs enter cells by different pathways, multi-drug resistance (MDR) can be minimized. Anticancer polymer-drug conjugates can be divided into two targeting modalities: passive and active. Tumor tissues have anatomic characteristics that differ from normal tissues. Macromolecules penetrate and passively accumulate preferentially in tumors relative to normal tissues, leading to extended pharmacological effects. This "enhanced permeability and retention" (EPR) effect is the principal reason for current successes with macromolecular anti-cancer drugs. Both natural and synthetic polymers have been used as drug carriers, and several bioconjugates have been clinically approved or are in human clinical trials. While clinically useful anti-tumor activity has been achieved using passive macromolecular drug delivery systems, further selectivity is possible by active targeting, such as thermal targeting with the elastin-like polypeptide. This strategy would augment the EPR effect, increase the specificity and efficacy of treatment, and reduce the cytotoxicity in normal tissues, thereby further improving the therapeutic index of the macromolecule-delivered drug.

As used herein, the term "tumor" or "tumors" comprises tumor cells and tumor stromal cells. Tumor stromal cells include tumor-supporting cells such as tumor vasculature endothelial cells, pericytes, tumor-associated macrophages and other tumor-associated tumor inflammatory cells.

As used herein, the terms "parenteral drug delivery", "parenteral therapeutic agent delivery" or "parenteral delivery" refer to delivery of therapeutic agents via routes other than enteral, where enteral includes only oral and rectal (into the gastrointestinal tract). The term parenteral includes, for example, intravenous, subcutaneous, intramuscular, intrathecal, intracerebral, intracerebral, and inhalation.

As used herein, the term "in combination" refers to the use of more than one prophylactic and/or therapeutic agents.

As used herein, the terms "manage," "managing" and "management" refer to the beneficial effects that a subject derives from the administration of a prophylactic or therapeutic agent, which do not result in a cure but the prevention of further progression or worsening of the disease or disorder.

As used herein, the terms "prevent," "preventing" and "prevention" refer to the deterrence of onset of the disease or disorder in a subject resulting from the administration of a prophylactic or therapeutic agent.

As used herein, the terms "prophylactic agent" and "prophylactic agents" refer to any agent(s) that can be used in the prevention of a disease or disorder.

As used herein, the term "prophylactically effective amount" refers to that amount of the prophylactic agent sufficient to prevent the onset of the disease or disorder.

As used herein, the term "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects include, but are not limited to, gastrointestinal toxicity, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, constipation, nerve and muscle effects, temporary or permanent damage to the heart, kidneys and bladder, flu-like symptoms, fluid retention, infertility problems, fatigue, dry mouth, loss of appetite, hair loss, rashes or swellings at the site of administration, flu-like symptoms such as fever, chills and fatigue, digestive tract problems, allergic reactions, depression, loss of appetite, eye problems, headache, and weight fluctuation. Additional undesired effects typically experienced by patients are numerous and known in the art (see e.g., Physicians' Desk Reference (56th ed., 2002)).

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, the terms "treat," "treating" and "treatment" refer to the amelioration or elimination of symptoms or recovering from the disease or disorder in a subject resulting from the administration of a therapeutic agent.

As used herein, the terms "therapeutic agent" and "therapeutic agents" refer to any agent(s) that can be used in the treatment of a disease or disorder.

As used herein, the term "therapeutically effective amount" refers to that amount of the therapeutic agent sufficient to reduce or minimize the symptoms of the disease or disorder and, preferably, result in the reduction in growth of tumor or cancer and/or survival of the subject.

As used herein, the terms "therapies" and "therapy" can refer to any protocol(s), method(s) and or agent(s) that can be used in the prevention, treatment, or management of diseases or disorder. In certain embodiments, the terms "therapy" and "therapies" refer to cancer chemotherapy, radiation therapy, hormonal therapy, biological therapy, and/or other therapies useful for the treatment of cancer, infectious diseases, autoimmune and inflammatory diseases known to a physician skilled in the art.

As used herein, the term "analog" refers to any member of a series of peptides having a common biological activity, including antigenicity/immunogenicity and antiangiogenic activity, and/or structural domain and having sufficient amino acid identity as defined herein.

As used herein, the term "variant" refers either to a naturally occurring allelic variation of a given peptide or a recombinantly prepared variation of a given peptide or protein in which one or more amino acid residues have been modified by amino acid substitution (preferably conservative), addition, or deletion.

As used herein, the term "derivative" refers to a variation of given amino acid, peptide or protein that are otherwise modified, i.e., by covalent attachment of any type of molecule, preferably having bioactivity, to the amino acid, peptide or protein, derivatives of an amino acid, including non-naturally occurring amino acids.

As used herein, the term "fragment" includes a peptide, polypeptide, or protein modified peptide polypeptide, protein or derivatives thereof, comprising an amino acid sequence of at least 3 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, at least contiguous 350 amino acid residues.

When referring to the administration of therapeutic agents or system of the present invention, the term "simultaneously" or "simultaneous" refers to the administration of two or more therapies or therapeutic agents within the same 24 hours period, whereas "sequentially" and "subsequently" are intended to mean that the therapeutic agents are separated by more than 24 hours, such as separated by days, weeks, months, years, depending on the effects of a particular therapeutic agent. In one preferred embodiment, "sequential" or "subsequent" refers to dosages that are separated by one day to six weeks.

A compound of the present invention can target a the tumor site by application of local hyperthermia. Hyperthermia preferentially increases the permeability of tumor vasculature compared to normal vasculature, which can further enhance the delivery of drugs to tumors. Using microwave, radiofrequency, or high-intensity focused ultrasound, hyperthermia has been introduced in the treatment of glioblastoma and head and neck cancer. Therefore, the methods and techniques necessary to ensure thermal targeting of the doxorubicin drug delivery polypeptide are in place.

Furthermore, the ELP-based doxorubicin carrier is capable of circumventing the most common pathway of drug resistance, a drug pumping mechanism that allows tumor cells to remove small molecule drugs and continue to survive in the presence of these drugs. To test the ability of the ELP doxorubicin carrier to overcome this drug resistance, a uterine cancer cell line (MES-SA) and its doxorubicin resistant subline MES-SA/Dx5 were treated with either free doxorubicin or ELP-delivered doxorubicin. Although the MES-SA/Dx5 cell line is 100 times more resistant to free doxorubicin as compared to MES-SA, the ELP-delivered doxorubicin is equally toxic to both the sensitive and resistant cell lines. This demonstrates that ELP-delivered doxorubicin may be used to overcome drug resistance.

A previous in vivo study of ELP delivery to human tumors implanted in nude mice demonstrated that hyperthermia of the tumor resulted in a two fold increase in tumor localization of a thermally responsive ELP compared to localization without hyperthermia. Over half of the increased accumulation could be attributed to the thermally triggered aggregation of the ELP, caused by the phase transition of the ELP in response to hyperthermia. These results suggest that enhanced delivery of drugs to solid tumors can be achieved by conjugation to thermally responsive polymers combined with local heating of tumors.

Chilkoti patented this observation, U.S. Pat. No. 6,582,926, disclosing that bioelastomers can be used in methods of binding compounds including immunoassay methods, in biosensors and methods of regenerating biosensors, and in methods for targeting the delivery of a compound to a particular location within animal subjects.

Major impediments to drug delivery in solid tumors are: (1) heterogeneous distribution of blood vessels, combined with aberrant branching and tortousity, which result in uneven and slowed blood flow; and (2) the high permeability of tumor vessels combined with the absence of a functional lymphatic system resulting in an elevated interstitial pressure, which retards convective transport of high MW (>2000 Da) drugs.

To increase efficacy of drug delivery and overcome these barriers, the present inventors modified the ELP sequence at its N-terminus by the addition of a membrane translocating sequence, a short peptide. In one embodiment, the HIV Tat protein, known to facilitate delivery of large cargo proteins across cell membranes, is used as the membrane translocating sequence. This peptide increases the amount of ELP that is internalized by cells. At the C-terminus, a cleavable tetrapeptide linker is added to the ELP sequence.

In one embodiment, the linker sequence, GFLG (SEQ ID NO: 3), is a substrate for the lysosmal protease Cathepsin B.

Additionally, in embodiments of the present invention, the C-terminal amino acid of the ELP drug carrier is a cysteine residue which is used for attachment of an agent such as, for example, a cytotoxic drug.

Examples of cytotoxic drugs which may be used in the present invention include: alkylating drugs, such as cyclophosphamide, ifospfamide, ehlorambucil, melphalan, busulfan, lomustine, carmustine, chlormethhine (mustine), estramustine, treosulfan, thiotepa, mitobronitol; cytotoxic antibiotics, such as doxorubicin, epirubicin, aclarubicin, idarubicin, daunorubicin, mitoxantrone (mitozantrone), bleomycin, dactinomycin and mitomycin; antimetabolites, such as methotrexate, capecitabine; cytarabine, fludarabine, cladribine, gemcitabine, fluorouracil, raltitrexed (tomudex), mercaptopurine, tegafur and tioguaninc; vinca alkaloids, such as vinblastine, vincristine, vindesine, vinorelbine and etoposide; other neoplastic drugs, such as amsacrine, altetarmine, crisantaspase, dacarbazine and temozolomide, hydroxycarbamide (hydroxyurea), pentostatin, platinum compounds including: carboplatin, cisplatin and oxaliplatin, porfimer sodium, procarbazine, razoxane; taxanes including: docetaxel and paclitaxel; topoisomerase I inhibitors including inotecan and topotecan, trastuzumab, and tretinoin.

In embodiments of the present invention, the cytotoxic drug is doxorubicin or a derivative thereof (dox).

Figure 2:
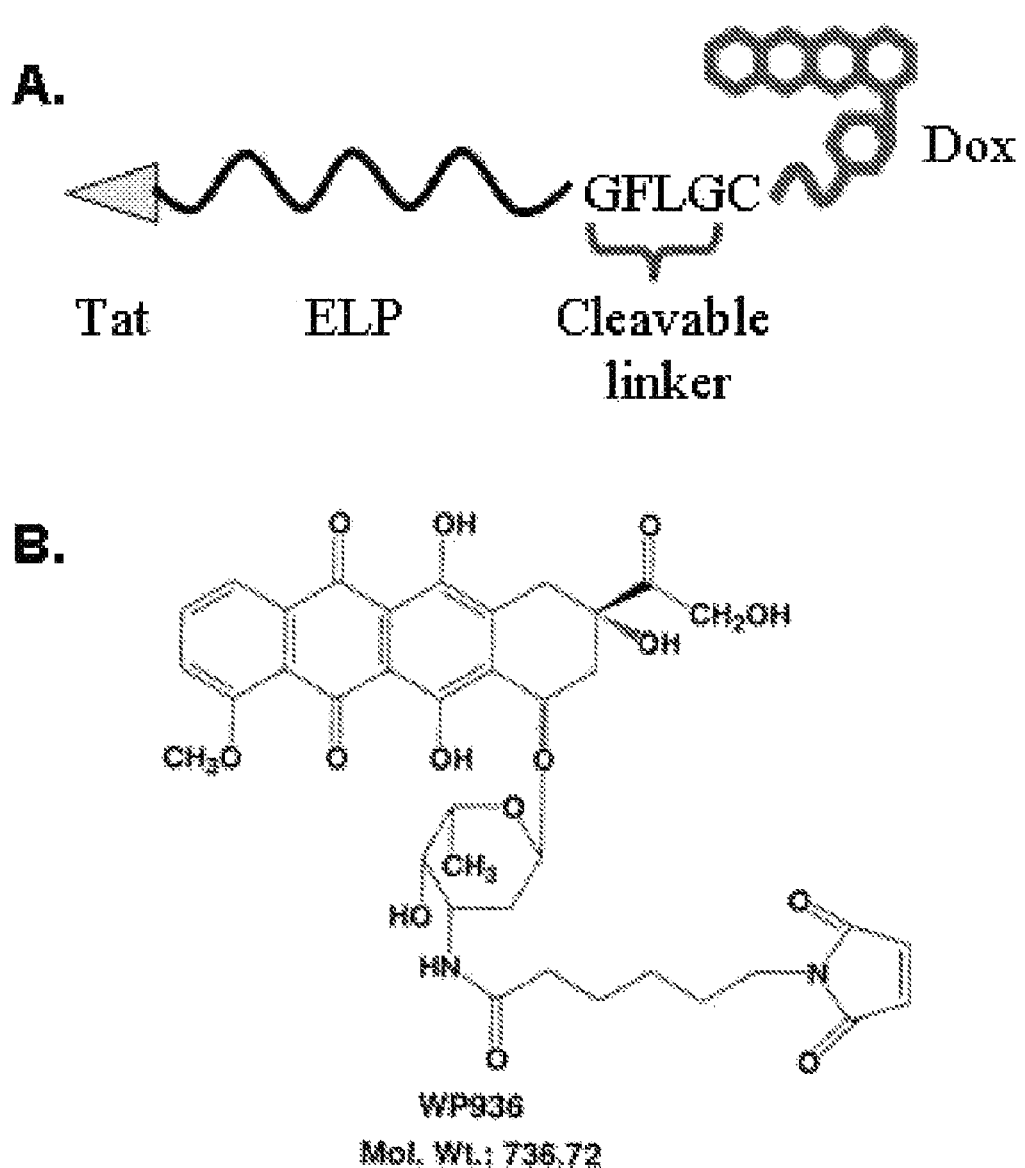
FIG. 2 shows an embodiment of a compound of the present invention. More specifically, FIG. 2 A shows an embodiment of a design of the ELP-based DOX delivery vehicle showing the Tat membrane translocating sequence, the cleavable GFLG peptide, and the attachment site for DOX. B shows the chemical structure of WP936, a thiol reactive analog of DOX. In the polypeptide identified in FIG. 2, GFLG is SEQ ID NO: 3 and GFLG with the C-terminal cystein is SEQ ID NO: 4.

See FIG. 2A for an embodiment of a compound of the present invention. Another compound of the present invention, a maleimide derivative of DOX is shown in FIG. 2B. In the figure, it is covalently attached to the cysteine sulfur. Without being bound by theory or mechanism, compounds of this embodiment, abbreviated Tat-ELP-GFLG-DOX (SEQ ID NO: 3), are taken in by the endosomal pathway, a process increased by the Tat peptide. Once internalized, the GFLG linker (SEQ ID NO: 3) are cleaved in the lysosomes, freeing the agent, in this example DOX, for action.

The present invention, including the doxorubicin carriers discussed in more detail below, has not only to targeting capability, but can overcome transport barriers to delivery, reach the molecular site of action within the cancer cells and inhibit their growth.

Additional examples of compounds of the present invention include the Tat-ELP polypeptide disclosed above with a cleavable linker. Additional compounds of the present invention include the polypeptides below and a cleavable linker.

| Polypeptides | Sequence |
|---|---|
| Antp-ELP[1] | MRQIKIWFQNRRMKWKK-(VPGXG)$_{120}$WP |
| Tat-ELP[2] | MYGRKKRRQRRR-(VPGXG)$_{120}$WP |
| MTS-ELP[3] | MAAVALLPAVLLALLAP-(VPGXG)$_{120}$WP |
| Bac-7-ELP[4] | MRRIRPRPPRLPRPRPRPLPFPRPG-(VPGXG)$_{120}$WP |
| Trans-ELP[5] | MGWTLNSAGYLLGKINLKALAALAKKIL-(VPGXG)$_{120}$WP |
| pVEC-ELP[6] | MLLIILRRRIRKQAHAHSK-(VPGXG)$_{120}$WP |

Additional compounds of the present invention include any of the above-disclosed compounds, wherein the cleavable linker sequence is GFLG (SEQ ID NO: 3).

Additional compounds of the present invention include any of the above-disclosed compounds conjugated with a therapeutic agent/anti-cancer agent (or derivative thereof) via the linker.

Additional compounds of the present invention include any of the above compounds with DOX or a DOX derivative.

The system of the present invention is capable of delivering a therapeutic agent to a tumor cell or a tumor-supporting cell in an increased amount compared to using traditional method of drug delivery. In certain embodiments, the delivery system comprises NGR-containing molecules linked to an encapsulating delivery vehicle, such as a liposome, that comprises a therapeutic agent, and is capable of delivering at least 0.5-2 folds, 2-5 folds, 5-10 folds, 15-20 folds, 20-30 folds, 30-40 folds, 40-50 folds, 50-100 folds more of the therapeutic agent to a targeted cell over a period of time as compared to other non-targeted drug delivery systems as well as targeted drug delivery systems. In specific embodiments, the tumor is exposed to over 2-10%, 10-20%, 20-30% 30-40%, 40-50%, 50-60%, 60-70%, 70-80%, 80-90%, or 90-99% of therapeutic agent over a period of at least 2-5 hours, 5-10 hours, 10-12 hours, 12-24 hours, 24-36 hours, 36-48 hours, 3-5 days, 5-7 days, or 1-3 weeks as compared to other delivery systems. Specifically, other parenteral delivery system. The amount of therapeutic agent present in a tumor cell or tumor-supporting cell may be determined by one skilled in the art or by methods used in Section 6 infra.

The methods of the invention include any therapeutic, prophylactic or diagnostic application that can benefit a subject. In certain embodiments, the invention is directed to methods for preventing, managing, treating or ameliorating cancer, angiogenesis, inflammation, cardiac conditions, or other diseases or disorders associated with endothelial cell proliferation by administering to a subject an effective amount of one or more disease-targeted drug delivery systems. In certain other embodiments, the invention is directed to methods for diagnosing or monitoring the presence or amount of vascular endothelial cells that, for example, expresses an NGR receptor. Pharmaceutical compositions and kits comprising the delivery systems are also encompassed.

As indicated below, the present invention is not limited to the delivery of doxorubicin. Genetically encoded synthesis enables the type, number, and location(s) of reactive sites, suitable for conjugation or chelation of drugs, to be precisely specified along the polymer chain. Therefore, a similar approach may be applied in design and synthesis of polypeptide carriers for chemotherapeutics with different intracellular targets. Examples of chemotherapeutic agents which may be coupled to the conjugate include, but are not limited to, methotrexate, vinblastine, taxol, etc. A more complete list is disclosed below.

Additional embodiments of the present invention include ELP-delivered peptides capable of inhibiting c-Myc oncogene activity and cyclin dependent kinase (cdk) activity. Other embodiments are not limited to c-Myc and cdk inhibition, but it may be applied to any oncogene or molecular target, by simply genetically modifying the existing ELP sequence. Such thermally responsive polypeptides, which are amenable to molecular design and engineering, are easily and inexpensively produced at high purity and quantity, and may be efficiently targeted and adapted to any cell type or tissue to further enhance specificity. Specific targeting of the proposed therapeutic polypeptides to solid tumors by local hyperthermia would increase specificity and efficacy of treatment and reduce the cytotoxicity in normal tissues. Thus, the polypeptide-mediated therapeutic delivery system of the present invention provides an alternative means to effectively substitute or augment present therapy for treatment of localized tumors.

Cancers and related disorders that can be treated, managed, prevented or diagnosed by the methods and compositions of the present invention include but are not limited to the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angio sarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma.

The methods and compositions of the invention are also useful in the treatment, management, prevention or diagnosis of hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosacoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes.

Additional types of cancer include neoblastoma, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). The tumor may be a solid tumor or a non-solid tumor and may be a primary tumor or a disseminated metastatic (secondary) tumor.

In specific embodiments, malignancy or dysproliferative changes (such as metaplasias and dysplasias), or hyperproliferative disorders, are treated or prevented in the ovary, bladder, breast, colon, lung, skin, pancreas, or uterus.

In other specific embodiments, the cancer is a breast tumor, melanoma, neuroblastoma, kidney cancer, or Kaposi's sarcoma.

The invention provides methods of preventing, managing, treating and ameliorating cancer, by administrating to a human or non-human animal an effective amount of a tumor-targeted drug delivery system. The targeted drug delivery systems of the invention may be administered to a subject per se or in the form of a pharmaceutical composition. The subject is preferably a mammal. The mammal can be a non-primate (e.g., cows, pigs, horses, cats, dogs, rats etc.) or a primate (e.g., monkey and human), most preferably a human. The human may be an adult, juvenile, infant, or fetus.

In certain embodiments, the delivery system is administered to the subject, concurrently with one or more other therapeutic or prophylactic composition useful for the treatment of cancer, angiogenesis, inflammation, a cardiac condition, or a disease or disorders associated with damaged or defective endothelial cells.

The term "concurrently" is not limited to the administration at exactly the same time, but rather administration in a sequence and within a time interval such that one or more therapeutic or prophylactic composition comprising the delivery system(s) can act together with another composition to provide an increased benefit than if they were administered otherwise. For example, each prophylactic or therapeutic composition may be administered at the same time or sequentially in any order at different points in time; however, if not administered at the same time, they should be administered sufficiently close in time so as to provide the desired therapeutic or prophylactic effect. Each composition can be administered separately, in any appropriate form and by any suitable route.

In other embodiments, the composition is administered before, concurrently or after surgery. Preferably the surgery completely removes localized tumors or reduces the size of large tumors. Surgery can also be done as a preventive measure or to relieve pain.

The agents that can be used in conjunction with the present invention include one of more angiogenesis inhibitors or angiolytic agents such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; 1-beta-D-arabinofuranosylcytosine ("AraC"); asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostano lone propionate; duazomycin; edatrexate; eflonithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; N-phosphonoacetyl-L-aspartate ("PALA"); pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; topotecan; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; amino levulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytotoxic factor; cytostatin; dacliximab; decitabine; dehydrodidemnin B; deslorelin; dexamethasone; dexifosfamide; dexrazoxane; dexverapamil; diaziquone; didenmin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfo sine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vincristine, vinxaltine; vitaxin; vorozole; zanoterone; zeniplatin; zilascorb; and zinostatin stimalamer.

A stated above, a specific embodiment of the present invention is the anti-cancer drug is doxorubin or a doxorubin-like compound. More specifically, ELP can serve as macromolecular carrier for thermally-targeted delivery of dox.

It has been shown previously that the endocytic uptake of a thermally responsive ELP is significantly enhanced by the thermally triggered phase transition of the polypeptide. This observation was confirmed in this study where it was shown that cellular uptake of the ELP-delivered Dox was enhanced by both the Tat peptide and hyperthermia. Interestingly, cellular uptake of ELP1-GFLG-Dox (SEQ ID NO: 3) was not significantly enhanced by heat treatment in the absence of the Tat peptide, even though both constructs undergo their phase transition in the 37 to 42° C. window. This result differs from previous reports of ELP1 labeled with fluorescein, in which as much as a 2 fold enhancement of cellular uptake with hyperthermia was seen in several different cell lines. A possible explanation is that the fluorescein dye is less hydrophobic than Dox, and therefore the large aggregates of ELP1-GFLG-Dox (SEQ ID NO: 3) may have a reduced affinity for the charged cell surface. Clearly, however, the addition of the Tat peptide increases the affinity of the large ELP aggregates for the cell membrane, as the uptake of Tat-ELP1-GFLG-Dox (SEQ ID NO: 3) was increased 3 fold at 37° C. and 6 fold at 42° C. as compared to ELP1-GFLG-Dox (SEQ ID NO: 3).

The cellular Dox levels resulting from Tat-ELP-GFLG-Dox (SEQ ID NO: 3) treatment were much lower than what results from treatment with free doxorubicin under similar conditions (data not shown). This reflects the disparate mechanisms by which the two molecules gain cellular entry. Free Dox is sufficiently small and hydrophobic to gain access to the intracellular environment by passive diffusion, while Tat-ELP-GFLG-Dox (SEQ ID NO: 3) relies on an active transport mechanism for cellular entry. This contrast in cellular uptake mechanisms of free and polymer bound Dox has been observed previously with HPMA delivered Dox. In the case of HPMA-Dox, the endocytic uptake is an advantage, leading to an alternative toxicity mechanism involving lipid peroxidation in cell membranes, enhanced tumor activity in vivo, lowered systemic toxicity, and the ability to overcome multidrug resistance.

The present invention demonstrates that the Tat-ELP-GFLG (SEQ ID NO: 3) delivered Dox does not localize to the nucleus. This is in contrast to the free drug, which localizes entirely in the nucleus where it serves as an intercalator and topoisomerase II poison. Similar to HPMA delivered Dox, Tat-ELP-GFLG (SEQ ID NO: 3) delivered Dox displayed a cytoplasmic distribution. The cause of this altered distribution may be the endocytic mode of cellular entry used by Tat-ELP-GFLG (SEQ ID NO: 3), the failure of Dox to be released from the ELP carrier, or the modifications made to the Dox structure. Interestingly, the Tat-ELP-GFLG (SEQ ID NO: 3)-delivered Dox is still cytotoxic regardless of its lack of nuclear localization, suggesting an alternate mechanism of toxicity for free and Tat-ELP-GFLG (SEQ ID NO: 3) delivered Dox. Tat-ELP-GFLG-Dox (SEQ ID NO: 3) also induced caspase activation more effectively than free Dox in spite of its less potent cytotoxicity, adding additional support to the hypothesis that the two forms of the drug are acting through different mechanisms. It has been shown that HPMA conjugated Dox causes alterations in plasma membrane permeability, induces lipid peroxidation, and induces both caspase dependent apoptosis and necrosis. Experiments are underway to determine the mechanism of cytotoxicity by Tat-ELP-GFLG (SEQ ID NO: 3) delivered Dox.

In embodiments of the present invention, free Dox was found to be much more potent than the ELP-delivered Dox. However, the cytotoxicity of the two agents can not be compared directly because of the different levels of drug in the cells. In fact, a previous study using HPMA delivered Dox found that, when corrected for intracellular drug levels, the cytotoxicity of polymer-delivered Dox was comparable to free Dox. Because of the complexities of drug pharmacokinetics and tissue distribution in vivo, the in vitro potency is a poor predictor of a drug's therapeutic value, especially when comparing a polymer-bound drug to the free drug. HPMA-Dox conjugates have been shown to have in vitro $IC_{50}$s in the micromolar range, much higher than the free Dox $IC_{50}$, but these HPMA-Dox conjugates have shown promise in preliminary clinical evaluations. The $IC_{50}$ values of HPMA-Dox and Tat-ELP-GFLG-Dox (SEQ ID NO: 3) are comparable, indicating that a therapeutic concentration of Tat-ELP-GFLG-Dox (SEQ ID NO: 3) is achievable.

A previous study by Dreher et al reported cytotoxicity with ELP delivered Dox in a squamous cell carcinoma line (FaDu). However, they did not observe enhancement of the cytotoxic effect with hyperthermia. Several differences between the Dreher et al work and this exist. First, Dreher et al used an acid-labile hydrazone linker for conjugation of the drug to ELP, which contrasts with the protease-cleavable linker used here. Second, the site of modification of Dox with the reactive moiety was different. Dreher et al used a multistep synthesis process to first introduce a reactive moiety into ELP, then attached Dox via the C-13 carbonyl group. In embodiments of the present invention, doxorubicin was modified by addition of a maleimide group via a linker to the amine nitrogen at C-3', allowing conjugation to a unique cysteine residue in a single step. Third, Dreher et al used the squamous cell carcinoma line (FaDu), while in this study, MES-SA uterine sarcoma cells were used. However, it is unlikely that these differences led to the enhancement of cytotoxicity by hyperthermia observed in this study. It is more likely that the thermally induced cytotoxicity reported here is due to the experimental conditions and to modification of ELP by addition of the cell penetrating peptide. In the Dreher et al study, cells were continuously exposed for 24 h or 72 h to ELP-Dox with hyperthermia applied only during the first hour, which would diminish the influence of hyperthermia. In embodiments of the present invention, the cells were exposed to both drug and hyperthermia for only 1 h in order to highlight the influence of hyperthermia treatment. During this time, the hyperthermia causes the protein to aggregate, and the polypeptide aggregates accumulate on the surface of the cell. As a result, there is an increase in the amount of polypeptide bound to the cells and eventually internalized by the cells when compared to soluble polypeptides at the normothermic temperature. The thermal enhancement observed by the inventors was also aided by the use of the Tat peptide. Some cytotoxicity was observed with the unlabeled Tat-ELP-GFLG (SEQ ID NO: 3) polypeptide, which is possibly due to the highly charged polymer's interaction with and disruption of the plasma membrane. The exact mechanism for this toxicity is under further evaluation. However, cell killing by Tat-ELP-GFLG-Dox (SEQ ID NO: 3) is not due simply to the toxicity of Tat-ELP-GFLG (SEQ ID NO: 3), as the unlabeled protein was an order of magnitude less potent than the Dox labeled construct and induced no caspase activation in the absence of Dox in MES-SA cell line The Tat peptide enhanced the cellular delivery of the large protein aggregates, as ELP1-GFLG-Dox (SEQ ID NO: 3) only showed a thermal targeting index of 2.85 compared to an index of 19.9 for Tat-ELP1-GFLG-Dox (SEQ ID NO: 3).

Examples of the present invention show that the use of ELP as a thermally targeted drug carrier for the intracellular delivery of doxorubicin. The Dox delivery construct underwent its phase transition at 40° C., and its internalization by cells was enhanced by both the use of a cell penetrating peptide and by its hyperthermia-induced phase transition. The ELP vector delivered Dox to the cell cytoplasm and killed cells by induction of apoptosis through a caspase dependent mechanism. The cytotoxicity was enhanced twenty-fold when treatment was combined with hyperthermia.

Preferably, the drugs/agents, or derivatives thereof will be attached to a cystine of a linker group of the present invention, or modified to attach to another reactive amino acid, lysine, for example.

The compositions can take the form of solutions, suspensions, emulsions, tablets, pills, capsules, powders, sustained-release formulations and the like, depending on the intended route of administration. Examples of routes of administration include parenteral, e.g., intra-arterial, intraportal, intramuscular, intravenous, intrathecal, intradermal, subcutaneous, transdermal (topical), transmucosal, intra-articular, intraperitoneal, and intrapleural, as well as intrathecal, intracerebral, inhalation and pulmonary administration. In another aspect, the delivery system and pharmaceutical composition are administered to the subject locally, for example, by injection to a local blood vessel which supplies blood to a particular tumor, organ, tissue, or cell afflicted by disorders or diseases.

For parenteral administrations, the composition comprises one or more of the following components: a sterile diluent such as water for injection, saline solution; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For injection, the delivery systems may be formulated in aqueous solutions, preferably in physiologically compatible buffers such as Hanks's solution, Ringer's solution, or physiological saline buffer. The solution may contain formulatory agents such as suspending, stabilizing and/or dispersing agents. In one embodiment, the delivery systems are formulated in sterile aqueous solutions.

For intravenous administration, suitable carriers include physiological saline, bacteriostatic water, or phosphate buffered saline (PBS). In all cases, the composition must be sterile and should be fluid to the extent that easy injectability with a syringe. It must be stable under the conditions of manufacture and storage and must be preserved against the contaminating action of microorganisms such as bacteria and fungi. The carrier can be a solvent or dispersion medium containing, for example, water, and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

The amount of compositions to be administered may vary. The skilled artisan will appreciate that certain factors may influence the dosage required to effectively treat a subject, including but not limited to the severity of the disease or disorder, previous treatments, the general health and/or age of the subject, if other diseases are present, the manner of administration and the judgment of the prescribing physician. The treatment can be a single treatment or a series of treatments. The therapy may be repeated intermittently while symptoms detectable or even when they are not detectable. It will also be appreciated that the effective dosage of nucleic acid molecule used for treatment may increase or decrease over the course of a particular treatment. Changes in dosage may result and become apparent from the results of diagnostic and monitoring assays as described herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans by allowing extrapolation of changes in pharmacokinetics and biodistribution observed in animal models to estimations of human doses.

Initial dosages can also be estimated from in vivo data, e.g., animal models, using techniques that are well known in the art. The dosage of such compositions lies preferably within a range of circulating concentrations that include the $ED_{50}$ with little or no toxicity. One skilled in the art could readily optimize administration to humans based on animal data, keeping in mind that encapsulating drug in a carrier can result in significant changes in the pharmacokinetics and biodistribution of the encapsulated drug.

Dosage amount and interval may be adjusted individually to provide levels of the drug at the disease site which are sufficient to maintain therapeutic effect. Levels in plasma may be measured, for example, by high performance liquid chromatography.

Usual patient dosages for administration by injection range from about 0.01 to 30 mg/kg/day, preferably from about 0.1 to 10 mg/kg/day, more preferably from 0.1 to 1 mg/kg body weight.

In one embodiment of the present invention, the dosages for administering the system of the present invention comprising doxorubicin is 0.1-1 mg/kg, two times a week, or 1-12 mg/kg once a week up to six weeks. In preferred embodiments, the dosages for administering the system of the present invention comprising vincristine is 0.1-1 mg/kg, two times a week, or 1-6 mg/kg once a week up to six weeks.

The delivery systems and/or pharmaceutical compositions of the invention can administered to a subject, sequentially or simultaneously, with surgery, standard and experimental chemotherapies, hormonal therapies, biological therapies, immunotherapies, radiation therapies, embolization, and/or chemoembolization therapies for the treatment or prevention of cancer.

The compositions as described herein can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

EXAMPLES

The following examples are set forth for exemplary purposes only, and show features of embodiments of the present invention. Accordingly, they are not to be construed as limiting of the present invention in any form.

Example 1

Thermal Properties of Polypeptides

In order to apply ELP-based polypeptides for drug delivery, a suitable temperature transition must be attained. The drug-labeled ELP should undergo its phase transition between 39 and 42° C., a temperature range sufficiently above normal body temperature to prevent unwanted systemic aggregation, but not hot enough to cause extensive toxicity. Elastin-like polypeptide is ideally suited as a thermally targeted drug carrier because the transition temperature can be easily manipulated by varying the molecular weight or the amino acid composition of the guest residue X in the VPGXG (SEQ ID NO: 2) sequence using simple molecular biology techniques. The transition temperature of Tat-ELP-GFLG-DOX (SEQ ID NO: 3) was assessed by monitoring the turbidity of a solution of the polypeptide while heating in physiological buffer. Tat-ELP1-GFLG-DOX (SEQ ID NO: 3) was found to have an ideal phase transition for drug delivery. The polypeptide is soluble and the solution is clear at physiological temperature (37° C.).

Figure 5:
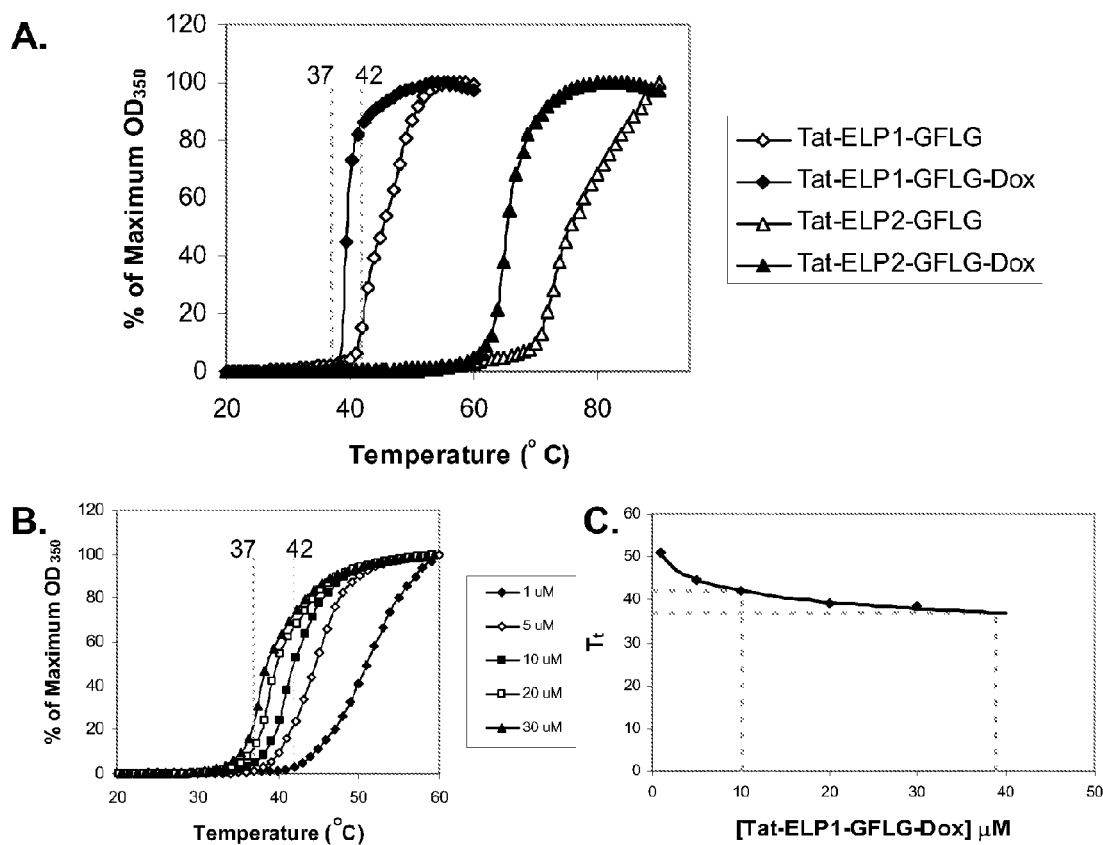
FIG. 5 shows the thermal properties of Dox delivery constructs. The turbidity of a 10 μM solution of labeled and unlabeled Tat-ELP-GFLG in PBS was monitored while the temperature was increased at a rate of 1° C./min (A). The effect of ELP concentration on the $T_t$ under cell culture conditions was determined by repeating the turbidity assay using concentrations of Tat-ELP1-GFLG-Dox ranging from 1 to 30 μM in cell culture media (B). Optical density (O.D.) data is converted to a percentage of the O.D. at 60° C. for each curve in order to view all concentrations on the same scale. The midpoint of the phase transitions in (B) were plotted versus the protein concentration and fit using a logarithmic equation ($R^2$=0.9942) in order to determine the concentration range in which the $T_t$ lies between 37° C. and 42° C. for Tat-ELP1-GFLG-Dox (C). In the polypeptides identified in FIG. 5, GFLG is SEQ ID NO: 3.

Temperature is raised to the hyperthermia temperature (42° C.), the polypeptide aggregates and the solution nears its maximum turbidity (FIG. 5A). Tat-ELP2-GFLG-DOX (SEQ ID NO: 3) is a polypeptide similar in size to Tat-ELP1-GFLG-DOX (SEQ ID NO: 3), but a different ELP moiety is incorporated. Tat-ELP2-GFLG-DOX (SEQ ID NO: 3) aggregates at a temperature significantly above the hyperthermia temperature, and it serves as a control to distinguish effects of the ELP phase transition from nonspecific hyperthermia-induced effects.

Example 2

Cellular Uptake of ELP-Delivered Doxorubicin

Figure 10:
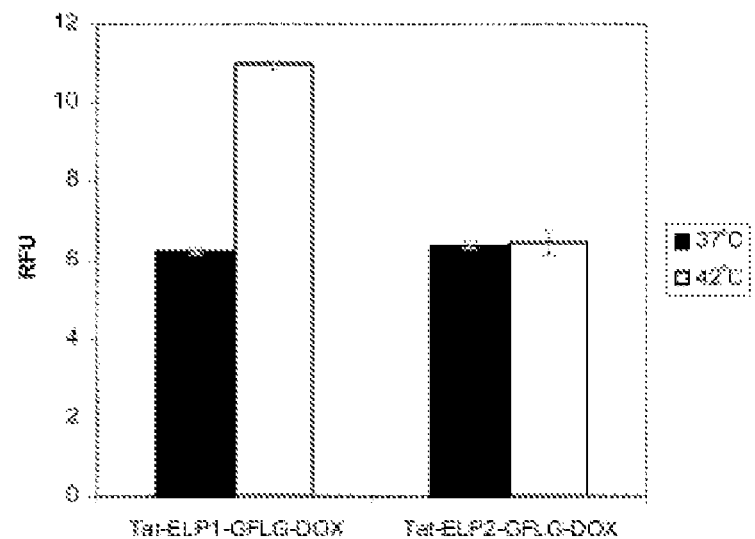
FIG. 10 shows the uptake of DOX delivered by ELP, as measured using the intrinsic DOX fluorescence and flow cytometry. Cells were treated with 10 μM Tat-ELP-GFLG (SEQ ID NO: 3)-DOX for 1 h at 37 or 42° C., and the DOX fluorescence was measured relative to standard beads.

In order to test whether the induction of ELP aggregation with hyperthermia can enhance the cellular uptake of the polypeptide, MES-SA uterine sarcoma cells were incubated with Tat-ELP-GFLG-DOX (SEQ ID NO: 3) for 1 h at either 37 or 42° C. Cells were then analyzed by flow cytometry, using the natural DOX fluorescence to quantify the amount of drug in the cells. When treated with the ELP1 containing construct, which aggregates at 40° C., the amount of drug delivered to the cells increases almost 2-fold (FIG. 10). On the other hand, uptake of the control construct which does not aggregate with hyperthermia was unaffected by heating to 42° C. This illustrates that the enhanced uptake observed after hyperthermia is the result of the ELP phase transition, not nonspecific effects of hyperthermia. This experiment demonstrates that the thermal properties of ELP may be used to increase the amount of drug delivered to a target cell.

Example 3

Inhibition of Cell Proliferation

Figure 11:
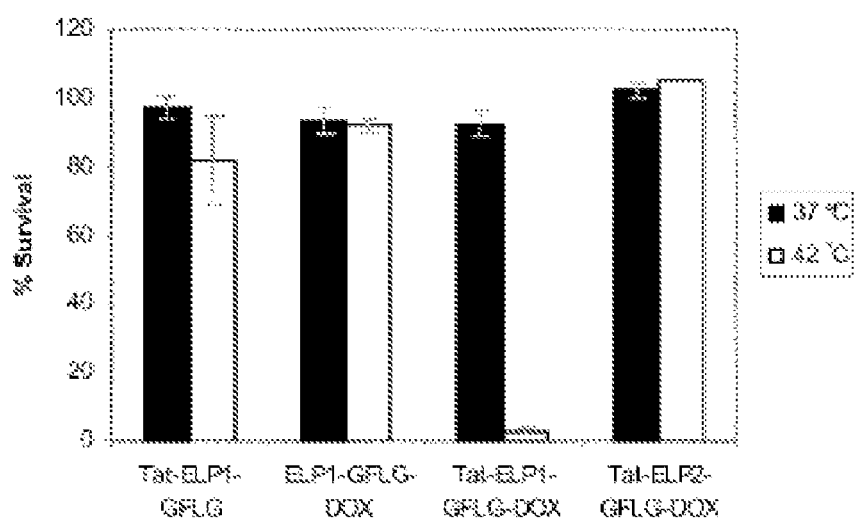
FIG. 11 shows the results of monitoring proliferation of MES-SA cells 72 H after a 1 h exposure to 5 μM polypeptides. GFLG (SEQ ID NO: 3). Cell number was assessed using a Coulter counter.

MES-SA cells were treated for 1 h at 37 or 42° C. with 5 µM Tat-ELP-GFLG-DOX (SEQ ID NO: 3); ELP-GFLG-DOX (SEQ ID NO: 3), which lacks the Tat cell penetrating peptide; or Tat-ELP-GFLG (SEQ ID NO: 3), which is not labeled with DOX. After the 1 h treatment, cells were rinsed and fresh media was replaced for 72 h. Cells remaining after 72 h were collected by trypsinization and counted using a Coulter counter. As shown in FIG. 11, the unlabeled Tat-ELP-GFLG (SEQ ID NO: 3) showed little toxicity to cells at either temperature. Similarly, the control polypeptide which lacks the Tat sequence was not cytotoxic, likely because it cannot efficiently enter the cells. Tat-ELP1-GFLG-DOX (SEQ ID NO: 3) showed little toxicity when treated at 37° C., where the polypeptide is soluble. However, treatment with Tat-ELP1-GFLG-DOX (SEQ ID NO: 3) at the hyperthermia temperature caused complete inhibition of cell proliferation. The control polypeptide Tat-ELP2-GFLG-DOX (SEQ ID NO: 3), which does not aggregate in response to hyperthermia, showed no thermal response and no cytotoxicity, similar to Tat-ELP1-GFLG-DOX (SEQ ID NO: 3) at 37° C. This data represents the first demonstration that ELP and hyperthermia may be used to deliver DOX to kill cells in a temperature dependent manner.

Example 4

Induction of Apoptosis with Tat-ELP-GFLG-DOX (SEQ ID NO: 3)

Figure 12:
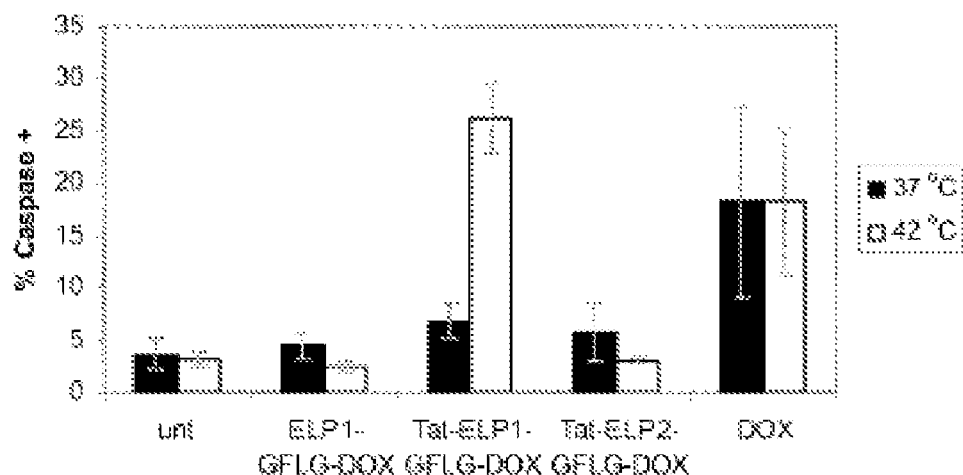
FIG. 12 shows the induction of Caspase activation by ELP-delivered DOX as measured 1 h after exposure to 10 μM ELP-DOX. GFLG (SEQ ID NO: 3). Active caspases were stained with a fluorescent caspase inhibitor and cells were analyzed using flow cytometry.

MES-SA cells were treated for 1 h at 37 or 42° C. with Tat-ELP-GFLG-DOX (SEQ ID NO: 3), the control construct lacking the Tat sequence, with free DOX. Cells were harvested after the 1 h exposure, and caspase activity was detected using a fluorescent caspase inhibitor (Immunochemistry Technologies, Bloomington, Minn.) and flow cytometry. No caspase activity was induced by hyperthermia alone, or by ELP-GFLG-DOX (SEQ ID NO: 3) (FIG. 12). When cells were treated at 37° C., Tat-ELP1-GFLG-DOX (SEQ ID NO: 3) and Tat-ELP2-GFLG-DOX (SEQ ID NO: 3) induced apoptosis slightly above control levels. However, when the treatment temperature was raised to 42° C., Tat-ELP1-GFLG-DOX (SEQ ID NO: 3) induced caspase activation in a significantly higher proportion of the population. Apoptosis induction by Tat-ELP2-GFLG-DOX (SEQ ID NO: 3) was not enhanced by hyperthermia, supporting the hypothesis that the higher levels of apoptosis seen with Tat-ELP1-GFLG-DOX (SEQ ID NO: 3) and hyperthermia are due to the ELP phase transition. Free DOX induced apoptosis under the conditions tested, but the levels were not affected by hyperthermia. Also, free DOX did not induce apoptosis as efficiently as the ELP-delivered DOX with hyperthermia.

Example 5

Proliferation of Tat-ELP-GFLG-DOX (SEQ ID NO: 3) in DOX Resistant Cells

Figure 13:
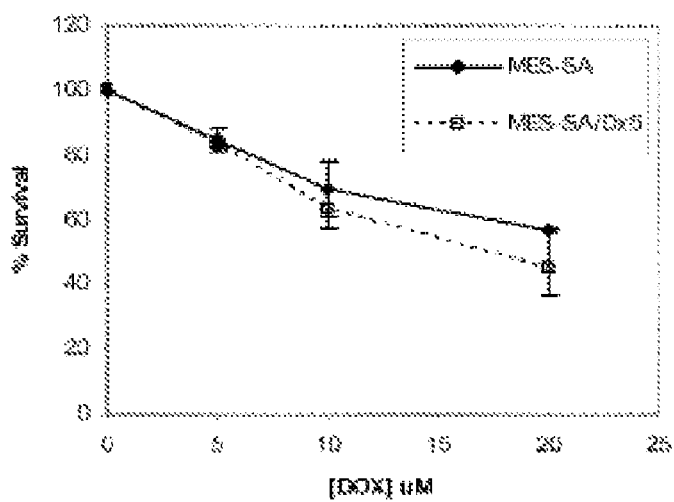
FIG. 13 shows proliferation of MES-SA and MES-SA/Dx5 cells treated with Tat-ELP-GFLG(SEQ ID NO: 3)-DOX. Cells were exposed to the polypeptide for 72 H, then counted using a Coulter counter.

A major problem with classical chemotherapy is the development of drug resistance. The most common mechanism of resistance is expression of a drug efflux pump (MDR1) by the cancer cells in response to drug treatment. This pump can remove drugs from the cells, and, though induced by one drug, it can act on a wide variety of others, resulting in a phenomenon called multi-drug resistance. Polymer delivered drugs are often able to bypass this drug pumping mechanism and overcome multi-drug resistance (12). MES-SA/Dx5 is a cell line selected for resistance to doxorubicin, and it also shows cross-resistance to many other drugs. The present inventors used this cell line to determine whether ELP delivered DOX can overcome MDR1-mediated resistance to doxorubicin. MES-SA/Dx5 cells were incubated with Tat-ELP-GFLG-DOX (SEQ ID NO: 3) continuously for 72 h. When treated with free DOX under these conditions, these cells can pump out the drug, and they are about 100-fold more resistant to free DOX than MES-SA cells. However, Tat-ELP-GFLG-DOX (SEQ ID NO: 3) shows similar cytotoxicity to both cell lines (FIG. 13). This result demonstrates that ELP delivered DOX may be able to circumvent the drug efflux pump.

Figure 3:
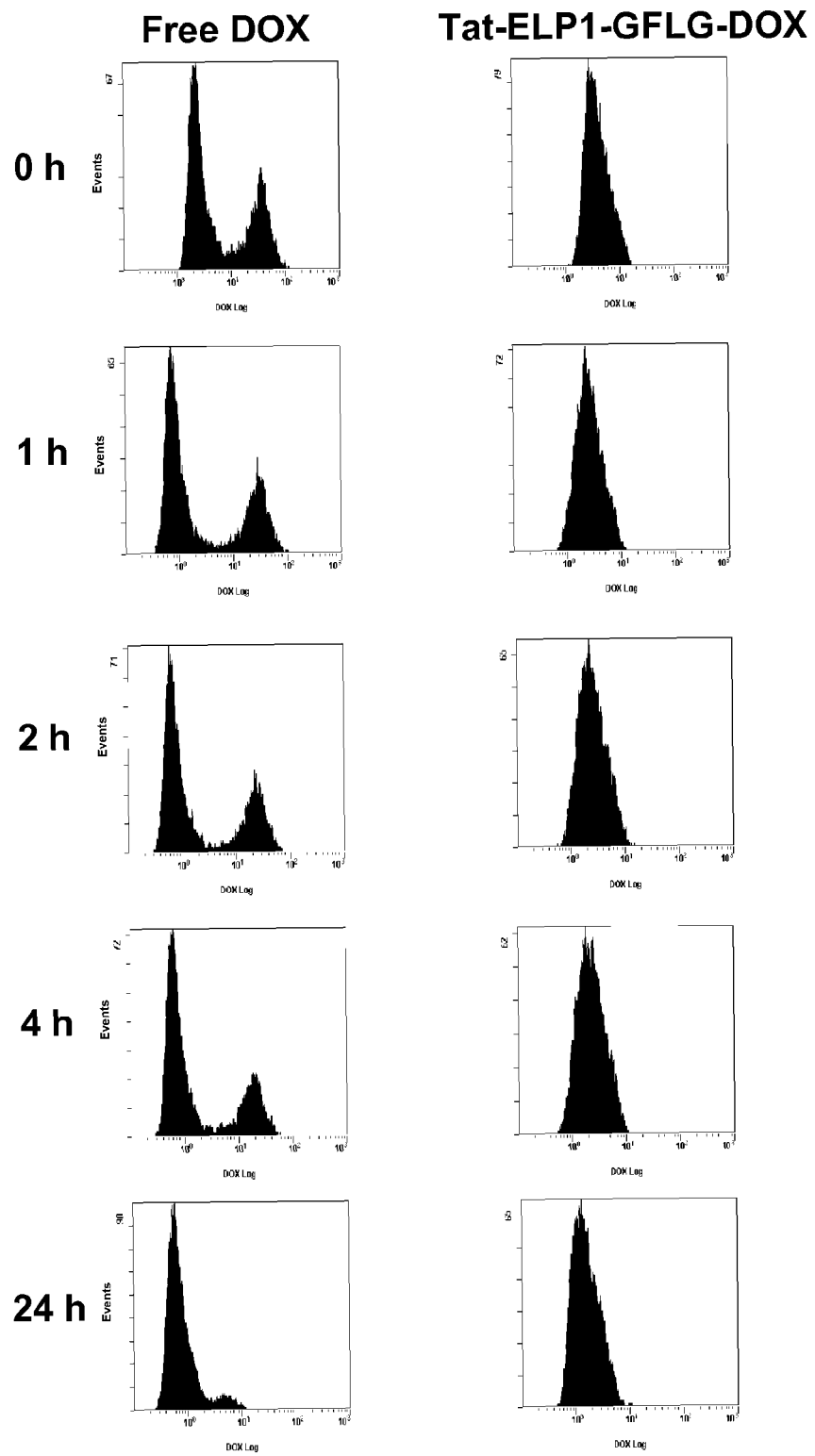
FIG. 3 shows the results of flow cytometry used to analyze drug efflux from cells treated with free DOX or with Tat-ELP-GFLG-DOX. More specifically, efflux of free DOX and Tat-ELP-GFLG-DOX from MES-SA/Dx5 cells was measured. Dx5 cells are drug resistant. Cells were loaded with about 10 μM DOX or ELP-DOX for about 5 h, the drug was removed, and DOX fluorescence was assessed at the indicated time points. This example shows, among other things, that Tat-ELP-GFLG-DOX can bypass the drug efflux pump. In the polypeptide identified in FIG. 3, GFLG is SEQ ID NO: 3.

For further evidence that Tat-ELP-GFLG-DOX (SEQ ID NO: 3) can bypass the drug efflux pump, flow cytometry was used to analyze drug efflux from cells treated with free DOX or with Tat-ELP-GFLG-DOX (SEQ ID NO: 3). Cells were loaded for 5 h with either 10 µM DOX or Tat-ELP-GFLG-DOX (SEQ ID NO: 3), then the drug was removed and fresh media was replaced. Cells were collected and analyzed for DOX content using flow cytometry. When treated with free DOX, the MES-SA/Dx5 cells show two populations (shown by the two peaks in the histogram in FIG. 3), one with high DOX fluorescence and one with low DOX fluorescence. The cells with low DOX fluorescence have pumped the drug out. As time passes after removal of the drug, the DOX positive peak gets lower in intensity and becomes a smaller percentage of the population. This illustrates the removal of DOX from theses cells with time after washing the drug out of the media. Contrasting this, Tat-ELP-GFLG-DOX (SEQ ID NO: 3) treated cells only show one peak in the flow cytometry histogram. This means that all cells have the same amount of drug in them. This single peak is still evident at all time points after removal of the drug. This means that these cells are unable to pump the ELP delivered DOX out. This result explains the observation that both cell lines are affected equally by Tat-ELP-GFLG-DOX (SEQ ID NO: 3), and it reveals the promise of ELP delivered DOX for overcoming multi-drug resistance in human therapy.

Example 6

ELP and Dox

Figure 4:
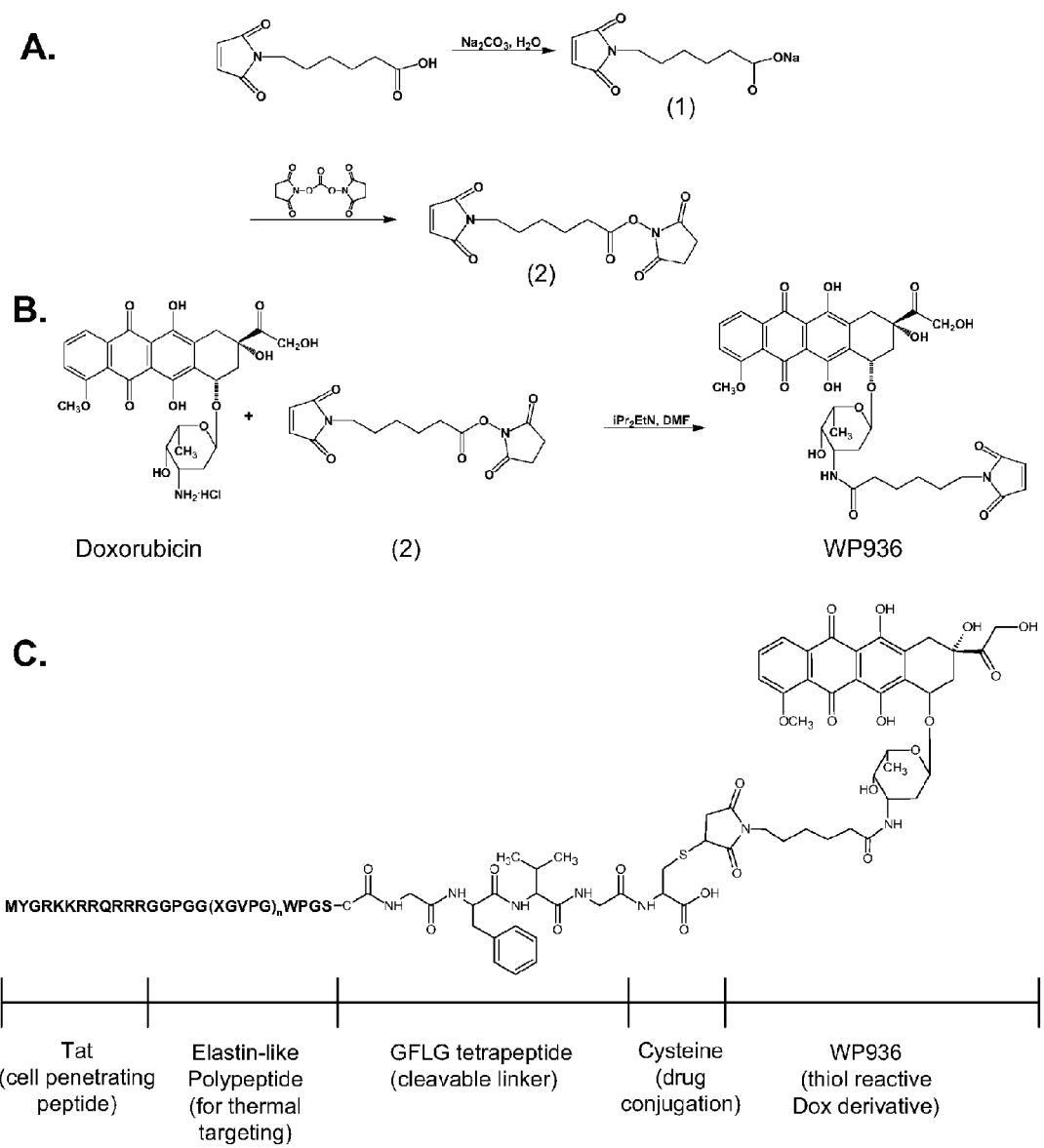
FIG. 4 shows the synthesis of N-succinimidyl ester of 6-maleimidocaproic acid (A). Synthesis of WP936, a thiol reactive derivative of doxorubicin (B). Schematic of the doxorubicin carrier polypeptide (C). The amino acid sequence of the Tat cell penetrating peptide and the ELP polypeptide are shown in single letter amino acid codes, and the chemical structure of the GFLG linker with the cysteine, which cysteine is conjugated to WP936 is shown. In the polypeptide identified in FIG. 4, Tat is SEQ ID NO:6, GGPGG is SEQ ID NO. 11, XGVPG is SEQ ID NO: 1, WPGS (SEQ ID NO: 12), and GFLGC is SEQ ID NO: 4.

Part 1: Materials and Methods 1.1. Synthesis of WP936, the Thiol Reactive Doxorubicin Derivative. N-succinimidyl ester of 6-maleimidocaproic acid was prepared as shown in FIG. 4A. The mixture of 6-maleimidocaproic acid (211 mg, 1 mmol) and sodium carbonate (50.3 mg, 0.5 mmol) in water (10 mL) was prepared and stirred at room temperature until all acid was dissolved. Water was evaporated to dryness. Residue was dissolved in methanol (10 mL), toluene (25 mL) was added, and solvents were evaporated to dryness. Addition and evaporation of the mixture of methanol and toluene was repeated three times. The obtained white powder of sodium salt (FIG. 4,(1)) was dissolved in ice-cold DMF (2 mL). N,N-dissuccinimidyl carbonate (281.8 mg, 1.1 mmol) was added and the reaction mixture was stirred at 0° C. for 1 hr. The reaction mixture was diluted with dichloromethane (25 mL), washed with water (3×15 mL), and dried over sodium sulfate. Inorganic salts were filtered off, solvents were evaporated to dryness, and residue was purified by column chromatography (SilicaGel 60, Merck) using dichloromethane as eluent, to give 184 mg of (2), yield 60%.

The mixture of Doxorubicin (hydrochloride salt) (38.4 mg, 0.065 mmol), (2) (30 mg, 0.08 mmol), diisopropylethylamine (28 μL, 0.16 mmol) and DMF (1 mL) was prepared and stirred at room temperature (FIG. 4B), while progress of the reaction was monitored by TLC (chloroform:methanol: ammonia=85: 15:2). After 40 min, the reaction was completed. The reaction mixture was diluted with dichloromethane (2 mL) and precipitated with hexanes (50 mL). The obtained solid was separated from solvents by centrifugation. The product was separated by column chromatography (SilicaGel 60, Merck) using chloroform, chloroform:methanol 98:2, 95:5 as eluents. Fractions containing WP936 were pooled together, evaporated to dryness, dissolved in chloroform (1 mL) and precipitated with hexanes (25 mL). The obtained solid was dried under vacuum to give 24 mg of WP936 (yield 60%). The $^1$H NMR spectrum was obtained for WP936 and was in agreement with the proposed structure.

$^1$H NMR (CDCl$_3$, δ) ppm: 14.0, 13.25 (2s, 1H ea, 6,11-OH), 8.04 (dd, 1H, J=7.6 Hz, J=0.7 Hz, H-1), 7.72 (dd, 1H, J=J=8.4 Hz, H-2), 7.4 (d, 1H, J=8.1 Hz, H-3), 6.67 (s, 2H, CH maleimid), 5.82 (d, 1H, J=8.6 Hz, NH), 5.50 (d, 1H, J=3.5 Hz, H-1'), 5.38 (bs, 1H, H-7), 4.76 (s, 2H, 14-CH$_2$), 4.56 (s, 1H, 9-OH), 4.16 (q, 1H, J=6.1 Hz, H-5'), 4.08 (s, 3H, OMe), 3.63 (bs, 1H, H-4), 3.49 (t, 2H, J=7.1 Hz, CH$_2$-linker), 3.28 (dd, 1H, J=18.8 Hz, J=1.8 Hz, H-10), 3.24 (d, 1H, J=18.8 Hz, H-10), 3.02 (m, 1H, H-3'), 2.34 (d, 1H, J=14.7 Hz, H-8), 2.17 (dd, 1H, J=14.7 Hz, J=4.1 Hz, H-8), 2.12 (dd, 2H, J=7.2 Hz, J=2.4 Hz, CH$_2$ from linker), 1.83 (dd, 1H, J=12.7 Hz, J=5.5 Hz, H-2' e), 1.78 (ddd, 1H, J=J=12.7 Hz, J=4.1 Hz, H-2' a), 1.63-1.55 (m, 4H, CH$_2$ from linker), 1.29 (d, 3H, J=6.1 Hz, H-6'), 1.30-1.25 (m, 2H, CH$_2$ from linker).

Anal. Elem. For $C_{37}H_{40}N_2O_{14} \times 2H_2O$ Calc. C, 57.51; H, 5.74; N, 3.63. Found: C, 57.90; H, 5.42; N, 3.60

1.2. Expression and Purification of ELP. The ELP1 and ELP2 gene sequences were graciously supplied by Dr. Chilkoti. Tat-ELP-GFLG (SEQ ID NO: 3) and other constructs used in this study were generated as described previously. All ELP constructs were expressed in *E. coli* using the hyperexpression system and purified by inverse transition cycling. Briefly, the *E. coli* strain BLR(DE3) containing the Tat-ELP-GFLG (SEQ ID NO: 3) construct in the pET 25b expression vector was grown for 24 h at 37° C. in Circle Grow media (Q-Biogene, Irvine, Calif.). The cells were lysed by sonication and, after precipitation of nucleic acids, Tat-ELP-GFLG (SEQ ID NO: 3) was precipitated from the soluble lysate by increasing the sodium chloride concentration and raising the temperature above the ELP $T_t$. The protein was collected by centrifugation, and this process was repeated until the desired purity was obtained as assessed by a single band on an SDS-PAGE gel.

1.3. Conjugation of ELP with WP936. A solution of ELP (ELP-GFLG (SEQ ID NO: 3) or Tat-ELP-GFLG (SEQ ID NO: 3)) was diluted to 100 μM in 50 mM Na$_2$HPO$_4$. Tris-(2-carboxyethyl)phosphine (TCEP; Molecular Probes, Eugene, Oreg.) was added to a 10 fold molar excess. WP936 was slowly added while mixing to a final concentration of 100 μM and incubated with continuous stirring overnight at 4° C. Unreacted label was removed by 3 inverse transition cycles [25] into PBS. Efficiency of labeling on the single cysteine residue was assessed by UV-visible spectrophotometry (modified from [21]). The typical molar label to protein ratio was 0.83±0.15.

1.4. Characterization of the Transition Temperature. The temperature induced aggregation of the proteins was characterized by monitoring absorbance at 350 nm while increasing the temperature. For initial analysis of Dox-labeled ELPs, solutions containing 10 μM protein in PBS were heated or cooled at a constant rate of 1° C./min in a temperature-controlled multicell holder in a UV-visible spectrophotometer (Cary 100, Varian instruments). The analysis was repeated with Tat-ELP1-GFLG-Dox (SEQ ID NO: 3) at concentrations ranging from 1 μM to 30 μM in cell culture media in order to determine the concentration dependence of the phase transition under experimental conditions. Absorbance data was converted to percentage of the maximal absorbance for each curve, and the $T_t$ was defined as the temperature at which the OD$_{350}$ reached 50% of the maximum turbidity. The concentration dependence of the $T_t$ was fit using a logarithmic equation.

1.5. Cell Culture and Polypeptide Treatment. MES-SA uterine sarcoma cells (ATCC, Manassas, Va.) were grown as a monolayer in 75 cm$^2$ tissue culture flasks and passaged every 3-5 days. MES-SA cells were grown in McCoy's 5A medium supplemented with 10% fetal bovine serum (FBS), 100 units/ml penicillin, 100 μg/ml streptomycin, and 25 μg/ml amphotericin B (Invitrogen, Carlsbad, Calif.). Cultures were maintained at 37° C. in a humidified atmosphere+5% CO$_2$. For experiments, cells were removed from tissue culture flasks by brief treatment with 0.05% v/v trypsin-EDTA (Invitrogen), plated in 6 well plates (300,000 cells/well for flow cytometry, 25,000 cells/well for proliferation) and allowed to grow for 24 h. Cells were treated with media containing polypeptides for 1 h at the indicated temperature, rinsed, and replaced with fresh media. In order to eliminate variability due to variation in labeling levels among different proteins or labeling batches, concentrations for cell treatments were always based on the Dox concentration as judged by the absorbance peak at 495 nm.

1.6. Polypeptide Uptake. Cells were treated with 20 μM Tat-ELP1-GFLG-Dox (SEQ ID NO: 3), Tat-ELP2-GFLG- Dox (SEQ ID NO: 3), or control polypeptides lacking the Tat sequence as described above. Duplicate plates were treated for 1 h at 37° C. and 42° C. Cells were rinsed with PBS and harvested using nonenzymatic cell dissociation buffer (Invitrogen), centrifuged for 2 min, and resuspended in 0.5 ml PBS. Total uptake of the doxorubicin labeled polypeptides was measured using the intrinsic Dox fluorescence by a Cytomics FC 500 flow cytometer (Beckman Coulter, Fullerton, Calif.). Forward versus side scatter gating was used to remove cell debris from the analysis, and Dox fluorescence was measured using FL3. Each histogram was a unimodal peak (n=5000 cells), and the peak mean was normalized to propidium standard beads.

1.7. Laser Scanning Confocal Fluorescence Microscopy. MES-SA cells were plated on 22 mm$^2$ cover slips at approximately 50% confluence and treated as described above with Tat-ELP-GFLG-Dox (SEQ ID NO: 3). Cells were rinsed with PBS at the indicated times, fixed with paraformaldehyde (PFA, 2% v/v) and visualized using a TCS SP2 laser scanning confocal microscope with a 100× oil immersion objective (Leica, Wetzlar, Germany). PMT voltages were lowered for imaging of cells treated at 42° C. during image acquisition to maximize image resolution and intensity. Therefore, the difference in image intensity between cells treated at 37° C. and 42° C. does not represent the actual difference in the amount of polypeptide in the cells.

1.8 Cytotoxicity Assay. Cells were plated and treated for 1 h at 37° C. and 42° C. as described above with Tat-ELP1-GFLG-Dox (SEQ ID NO: 3), Tat-ELP2-GFLG-Dox (SEQ ID NO: 3), or control polypeptides lacking the Tat sequence or unlabeled with Dox. Cells were rinsed and harvested 72 h after treatment by trypsinization, collected by centrifugation, and resuspended in isotonic buffer. Cell number was determined using a Coulter counter and expressed as a percentage of untreated cells.

1.9. Apoptosis Assays. For differential interference contrast (DIC) microscopy, MES-SA cells were plated onto 22 mm$^2$ coverslips at 50% confluence. Cells were treated as described above with the indicated protein, rinsed with PBS, and mounted onto glass slides. The unfixed cells were imaged immediately using a Zeiss Axiovert 200 DIC microscope with a 40× oil immersion objective and a Coolsnap HQ camera.

Caspase activation was measured using a carboxyfluorescein FLICA polycaspase assay (Immunochemistry Technologies, Bloomington, Minn.). Cells were treated as described above with the indicated protein, collected by trypsinization, and stained for 2 h at 37° C. with the carboxyfluorescein FLICA reagent as described by the manufacturer. Cells were rinsed twice and analyzed for caspase activation by flow cytometry using a Cytomics FC 500 flow cytometer (n=5,000 cells). Forward versus side scatter gating was used to eliminate cell debris from the analysis, and a histogram of fluorescein fluorescence (channel FL1) was bimodal with peaks for caspase positive and caspase negative cells. The percentage of caspase positive cells was determined from the histograms and expressed as an average of 3 experiments.

1.10. Data Fitting and Statistical Analysis. The concentration dependence of the $T_t$ was fit with a logarithmic equation using Microsoft Excel. Dose-response curves were fit using exponential or sigmoid equations as applicable using Microcal Origin in order to determine the 50% inhibitory concentration ($IC_{50}$). The thermal targeting index was calculated for each construct by dividing the $IC_{50}$ at 37° C. by the $IC_{50}$ at 42° C. The significance of the thermal targeting index was assessed by comparing the normothermia group with the hyperthermia group using a paired Student's t-test in Microsoft Excel. p values of less than 0.05 were considered statistically significant. Polypeptide uptake and caspase activation were analyzed for statistical differences using one-way ANOVA analyses with post-hoc Scheffe's tests for pair-wise comparisons of treatment groups. The statistical significance level was p<0.05.

Part 2. Experimental Results 2.1. Design, Synthesis, and Conjugation of Tat-ELP-GFLG (SEQ ID NO: 3) and WP936. The ELP drug delivery vector is composed of the pentapeptide repeat XGVPG (SEQ ID NO: 1), and it is designed to undergo a phase transition when the temperature is raised above its characteristic $T_t$. Two versions of the Dox delivery vector were made using two different ELP repeats. The ELP1-based construct contains 150 pentapeptide repeats (MW=59.1 kDa) with the guest position comprised of the amino acids V, G, and A in a 5:3:2 ratio. ELP1 was designed to have a $T_t$ just above physiologic temperature for use as a thermally targeted vector. A second polypeptide was constructed including ELP2, which contains 160 XGVPG (SEQ ID NO: 1) repeats (MW=61 kDa), where X is represented by V, G, and A in a 1:7:8 ratio. ELP2 has a similar molecular weight to ELP1, but it does not undergo its phase transition during the mild hyperthermia used in this study. Thus it serves as a non-thermally responsive control for the effects of hyperthermia. Tat-ELP-GFLG (SEQ ID NO: 3) was designed to include the Tat cell penetrating peptide to allow cellular entry of the macromolecular construct, and the GFLG (SEQ ID NO: 3) tetrapeptide linker was included to allow intracellular drug release by lysosomal proteases. The C-terminal amino acid of the vector is a cysteine, which provides a chemically reactive thiol group for drug conjugation. WP936 is a thiol reactive Dox derivative obtained by conjugating a maleimido moiety via a linker with the amino group at the C-3' position (FIGS. 4A and B). WP936 can be covalently attached to the cysteine sulfur by nucleophilic addition. The labeling reaction resulted in an average molar ratio of Dox:protein of 0.83±0.15. The amino acid sequence and chemical structure of WP936 covalently bound to the sulfur atom of the C-terminal cysteine is shown in FIG. 4C.

3.2. Thermal Properties of the Dox Delivery Vector. In order to apply ELP-based polypeptides for drug delivery, a suitable temperature transition must be attained. The drug-labeled ELP should undergo its phase transition between 39° C. and 42° C., a temperature range sufficiently above normal body temperature to prevent unwanted systemic aggregation. This temperature range is preferred for clinical applications of hyperthermia because it minimizes the incidence of edema and necrosis in healthy tissue surrounding a heated tumor. Elastin-like polypeptide is ideally suited as a thermally targeted drug carrier because the $T_t$ can be easily manipulated by varying the molecular weight or the amino acid composition of the guest residue X in the XGVPG (SEQ ID NO: 1) sequence using simple molecular biology techniques. The $T_t$ of Tat-ELP-GFLG-Dox (SEQ ID NO: 3) was assessed by monitoring the turbidity of a 10 μM solution of the polypeptide while heating in PBS. The $T_t$ of Tat-ELP1-GFLG (SEQ ID NO: 3) was found to be 46° C. However, labeling the polypeptide with Dox caused a significant downshift in the $T_t$ (FIG. 5A), and as a result, Tat-ELP1-GFLG-Dox (SEQ ID NO: 3) had an ideal phase transition for drug delivery ($T_t$=40° C.). The polypeptide was soluble and the solution was clear at physiological temperature (37° C.), but when the temperature was raised to the hyperthermia temperature (42° C.), the polypeptide aggregated and the solution approached its maximum turbidity. Tat-ELP2-GFLG-Dox (SEQ ID NO: 3) is a polypeptide similar in size to Tat-ELP1-GFLG-Dox (SEQ ID NO: 3), but a different ELP moiety is incorporated. Tat-ELP2-GFLG-Dox (SEQ ID NO: 3) aggregates at a temperature significantly above the hyperthermia temperature ($T_t$=65° C.), and it serves as a control to distinguish effects of the ELP phase transition from nonspecific hyperthermia-induced effects.

The phase transition of ELP is inversely related to the concentration of ELP and is also influenced by the concentration of other co-solutes. Therefore, in order to test the concentration range in which the Tat-ELP1-GFLG-Dox (SEQ ID NO: 3) $T_t$ is in the desired temperature range of 37 to 42° C., the turbidity assay was repeated with various concentrations of Tat-ELP1-GFLG-Dox (SEQ ID NO: 3) in cell culture media containing 10% FBS (FIG. 5B). The $T_t$ was determined for each curve, and a plot of $T_t$ versus polypeptide concentration revealed an inverse relationship which was best fit using a logarithmic function (FIG. 5C). This analysis showed that the midpoint of the phase transition was in the desired temperature range for concentrations between 10 and 39 μM. It should be noted, however, that some aggregation does occur at 42° C. for concentrations lower than 10 μM. Therefore, some thermal effect may be seen for cells treated under these conditions. The Tat-ELP-GFLG-Dox (SEQ ID NO: 3) concentration is an important characteristic for thermal targeting because if the concentration of the ELP carrier is too high, it will undergo its phase transition at normal physiological temperature.

Figure 6:
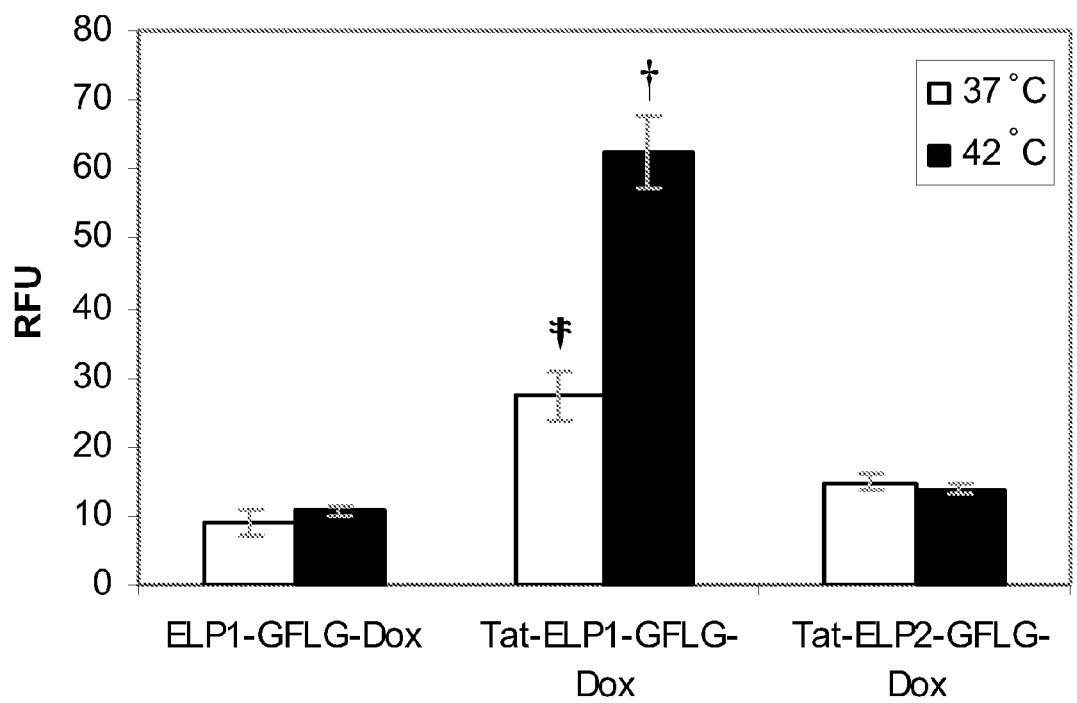
FIG. 6 shows cellular Uptake of Dox labeled ELP. MES-SA uterine sarcoma cells were incubated with Dox labeled constructs (20 μM in cell culture media) for 1 h at 37° C. or 42° C. The Dox fluorescence intensity was determined using flow cytometry and is expressed in relative fluorescence units (RFU). The data represents the mean of at least 3 experiments (error bars, SEM). ‡, significant difference compared with ELP1-GFLG-Dox at 37° C. †, significant difference compared with Tat-ELP1-GFLG-Dox at 37° C. (p<0.0001, one was ANOVA, p<0.05, Scheffe's test). In the polypeptides identified in FIG. 6, GFLG is SEQ ID NO: 3.

3.3. Cellular Uptake of ELP-delivered Doxorubicin. MES-SA uterine sarcoma cells were used in this study to evaluate the efficiency of ELP-mediated cellular delivery of doxorubicin. MES-SA cells were incubated with 20 μM Tat-ELP-GFLG-Dox (SEQ ID NO: 3) or a control polypeptide which lacks the Tat sequence for 1 h at either 37° C. or 42° C. After harvesting the cells with non-enzymatic cell dissociation buffer to prevent degradation of polypeptide attached to the cell surface, the non-fixed cells were analyzed by flow cytometry to measure the Dox fluorescence. This assay provides information about the total amount of Dox associated with the cells, both internalized and bound to the cell membrane. FIG. 6 shows that in the absence of the Tat peptide, low levels of ELP were associated with the cells at either temperature. However, cell association and uptake of Tat-ELP1-GFLG-Dox (SEQ ID NO: 3) was increased over 3 fold as compared to ELP1-GFLG-Dox (SEQ ID NO: 3) when cells were treated at 37° C. ($p<0.05$). In addition, hyperthermia further enhanced the association and uptake of Tat-ELP1-GFLG-Dox (SEQ ID NO: 3). Cellular fluorescence was increased over 2 fold when the MES-SA cells were treated with Tat-ELP1-GFLG-Dox (SEQ ID NO: 3) at 42° C. rather than 37° C. ($p<0.05$). Levels of Tat-ELP2-GFLG-Dox (SEQ ID NO: 3), the non-thermally responsive control polypeptide, were unaffected by treatment with hyperthermia. This supports the hypothesis that the additional cellular association observed with Tat-ELP1-GFLG-Dox (SEQ ID NO: 3) and hyperthermia is due to the polypeptide phase transition and not to non-specific effects of hyperthermia.

Figure 7:
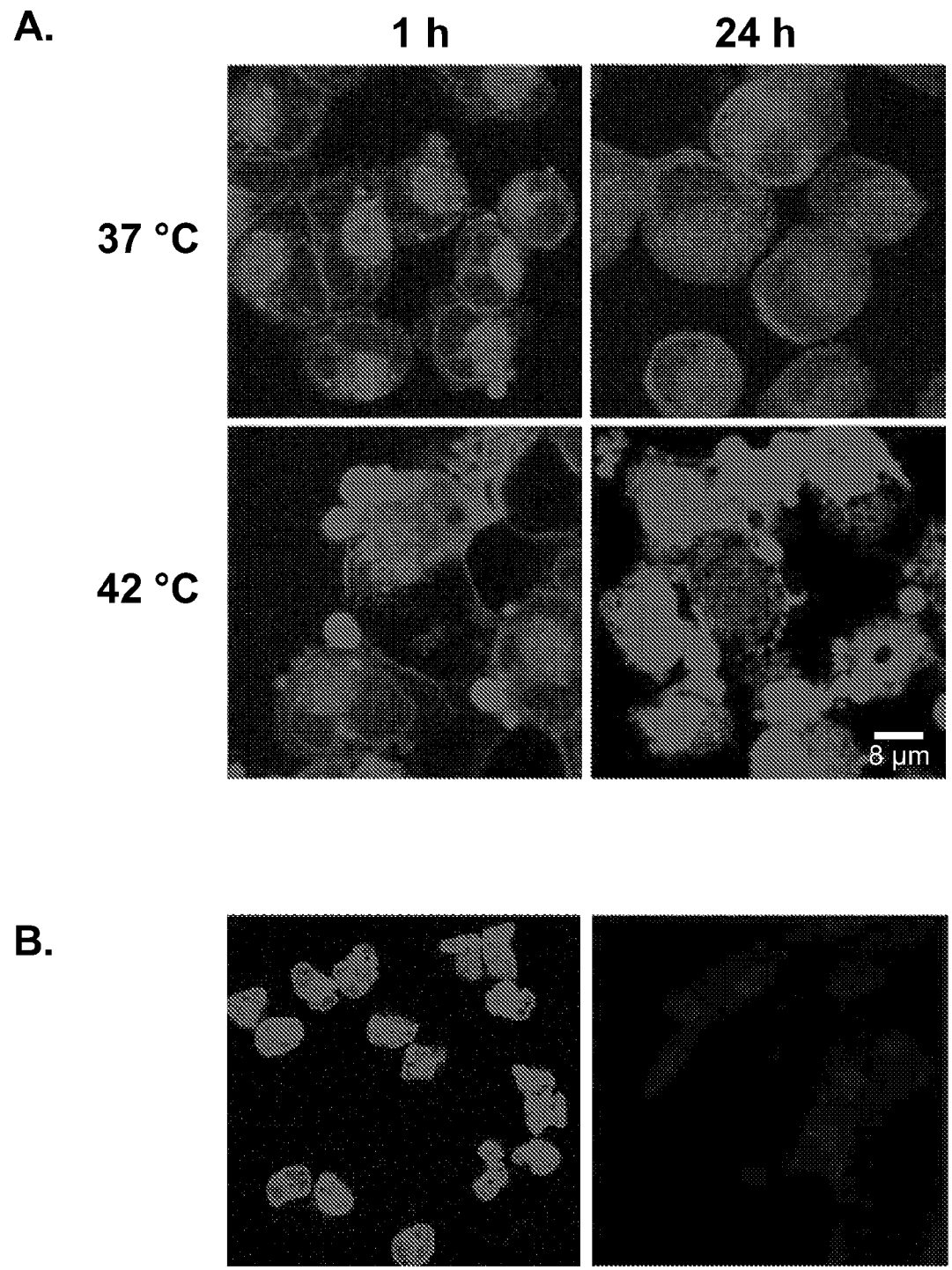
FIG. 7 shows intracellular localization. Confocal fluorescence images of MES-SA cells were collected 1 h and 24 h after a 1 h exposure to Tat-ELP1-GFLG-Dox (SEQ ID NO: 3) (10 μM in cell culture media) at 37° C. or 42° C. (A). PMT voltages were decreased for collection of 42° C. images. Therefore, the image intensity does not reflect the actual level of Dox in the cells. Control cells were treated with free Dox (10 μM in cell culture media) (left panel) or untreated to check for autofluorescence (right panel) (B).

3.4. Cellular Distribution. To confirm that Tat-ELP-GFLG-Dox (SEQ ID NO: 3) was internalized and not merely attached to the cell exterior, the cellular distribution of the ELP-delivered drug was examined by confocal fluorescence microscopy. MES-SA cells were treated for 1 h at 37° C. and 42° C. with 10 μM Tat-ELP1-GFLG-Dox (SEQ ID NO: 3). The cells were rinsed and analyzed immediately after treatment and 24 h later using the intrinsic Dox fluorescence. Taking a confocal section through the center of the cells confirmed internalization of Tat-ELP1-GFLG-Dox (SEQ ID NO: 3) immediately after treatment, with the drug accumulating in the plasma and nuclear membranes as well as in a punctate pattern in the cytoplasm (FIG. 7A, top, left). When Tat-ELP1-GFLG-Dox (SEQ ID NO: 3) treatment was combined with hyperthermia, the membrane and cytoplasmic distribution was still present, but the protein was present in large aggregates and the cells had begun to show hallmarks of apoptosis including rounding and membrane blebbing (FIG. 7A, bottom, left). 24 h after treatment, the ELP-delivered Dox still remained in the cell cytoplasm, and it displayed a more diffuse distribution (FIG. 7A, top, right). The cells observed 24 h after Tat-ELP1-GFLG-Dox (SEQ ID NO: 3) treatment combined with hyperthermia again showed accumulation of the large ELP-drug aggregates in a diffuse cytoplasmic distribution and extensive apoptosis (FIG. 7A, bottom, right). In contrast to the ELP-delivered doxorubicin, the free drug was found exclusively in the cell nucleus (FIG. 7B, left panel). Untreated cells had no signal under the imaging settings used, ruling out any contribution to the images from autofluorescence (FIG. 7B, right panel).

Figure 8:
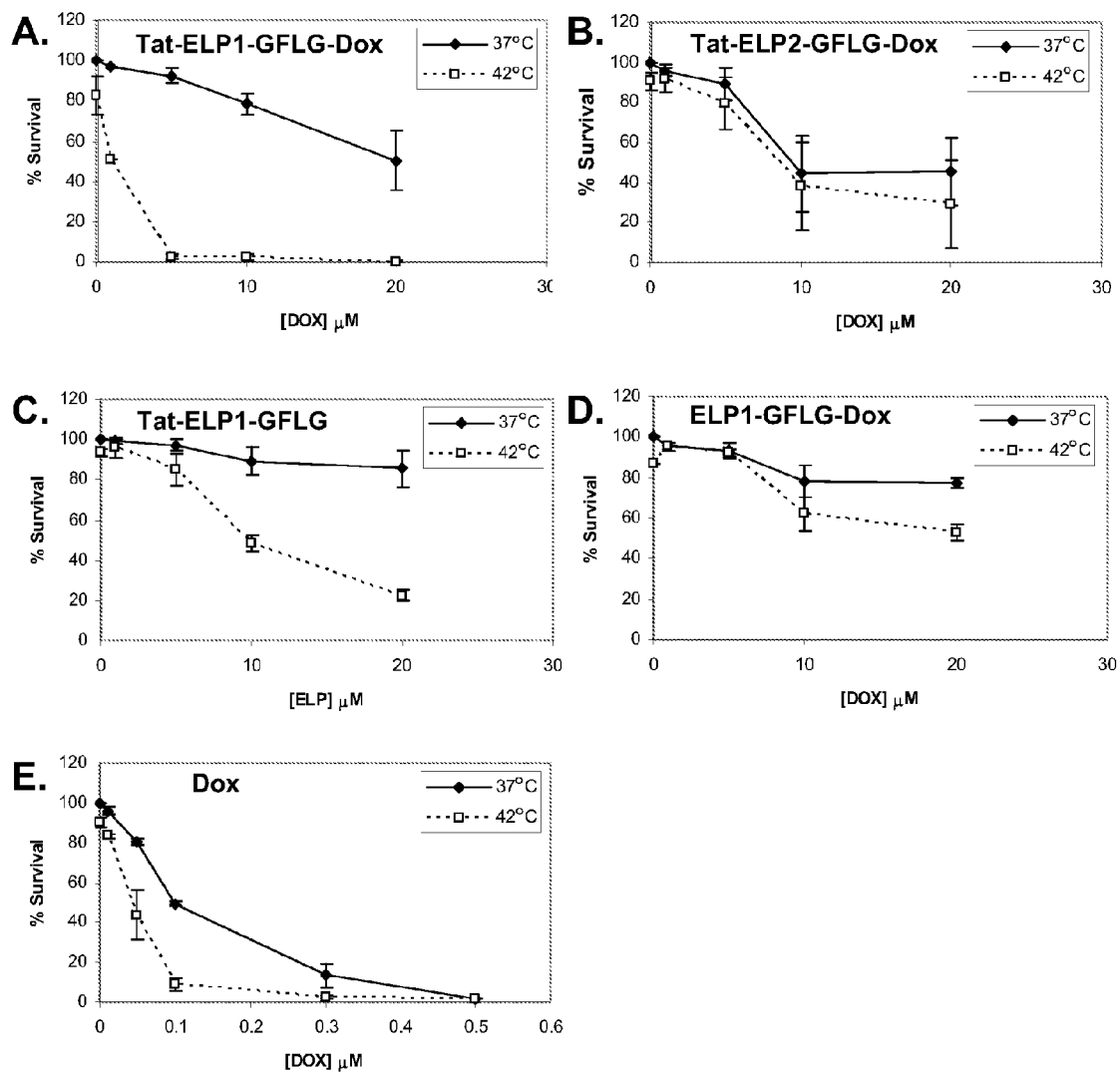
FIG. 8 shows cell proliferation. MES-SA cells were exposed to varying concentrations of Tat-ELP 1-GFLG-Dox (A), Tat-ELP2-GFLG-Dox (B), Tat-ELP1-GFLG (C), ELP1-GFLG-Dox (D), or free Dox (E) for 1 h at 37° C. or 42° C., and cells were counted after 72 h. The data represent an average of at least 3 experiments (bars, SEM). In the polypeptides identified in FIG. 8, GFLG is SEQ ID NO: 3.

3.5. Cytotoxicity of ELP-delivered Dox. The growth-inhibitory activity of Tat-ELP-GFLG-Dox (SEQ ID NO: 3) was evaluated in the MES-SA uterine sarcoma cell line. MES-SA cells were treated for 1 h at 37° C. or 42° C. with various concentrations of Tat-ELP-GFLG-Dox (SEQ ID NO: 3); ELP-GFLG-Dox (SEQ ID NO: 3), which lacks the Tat cell penetrating peptide, the Tat-ELP-GFLG (SEQ ID NO: 3) polypeptide without Dox; or free Dox. After the 1 h treatment, the cells were rinsed and fresh media was replaced for 72 h. Cells remaining after 72 h were rinsed, collected by trypsinization, and counted using a Coulter counter. FIG. 8A shows that Tat-ELP1-GFLG-Dox (SEQ ID NO: 3) was cytotoxic at 37° C., but high concentrations were needed. However, when Tat-ELP1-GFLG-Dox (SEQ ID NO: 3) was applied in combination with hyperthermia, the cytotoxicity was greatly enhanced. Tat-ELP2-GFLG-Dox (SEQ ID NO: 3) was also cytotoxic (FIG. 8B), but the toxicity was not affected by hyperthermia and was similar to Tat-ELP1-GFLG-Dox (SEQ ID NO: 3) at 37° C. The toxicity of the unlabeled Tat-ELP-GFLG (SEQ ID NO: 3) protein was negligible when treated below the $T_t$. However, Tat-ELP1-GFLG (SEQ ID NO: 3) did show some toxicity at high concentrations when treated at 42° C., but this nonspecific toxicity did not approach the toxic levels observed with the Dox labeled protein (FIG. 8C). ELP1-GFLG (SEQ ID NO: 3) Dox exhibited very poor potency at either treatment temperature, which is consistent with its poor cellular uptake in the absence of the Tat peptide (FIG. 8D). Free Dox was more cytotoxic than the polymer-delivered drug (FIG. 8E), which reflects its passive cellular entry and is consistent with other studies of Dox bound to synthetic polymers. The Dox toxicity was also affected by hyperthermia, which is likely due to enhanced diffusion of the drug into the cells.

For direct comparison of the cytotoxic effects of the Dox delivery constructs, each data set was fitted to an exponential or sigmoid equation to determine the $IC_{50}$ value. Additionally, the thermal targeting index was calculated by dividing the $IC_{50}$ of each polypeptide at 37° C. by its $IC_{50}$ at 42° C., and presented in Table 6, below:

TABLE 1

| IC$_{50}$ values for all ELP-doxorubicin constructs | | | |
| --- | --- | --- | --- |
| Construct | $IC_{50}$ (37° C.) (μM ± SEM) | $IC_{50}$ (42° C.) (μM ± SEM) | Thermal Targeting Index ($IC_{50}^{37°}/IC_{50}^{42°}$) |
| Dox | 0.130 ± 0.01 | 0.058 ± 0.02 | 2.3 † |
| Tat-ELP1-GFLG | 45.1 ± 12 * | 10.1 ± 0.36 | 4.47 † |

TABLE 1-continued

IC$_{50}$ values for all ELP-doxorubicin constructs

| Construct | IC$_{50}$ (37° C.) (μM ± SEM) | IC$_{50}$ (42° C.) (μM ± SEM) | Thermal Targeting Index (IC$_{50}^{37°}$/IC$_{50}^{42°}$) |
|---|---|---|---|
| (SEQ ID NO: 3) ELP1-GFLG-Dox | 44 ± 8 * | 15.4 ± 3.9 | 2.85 † |
| (SEQ ID NO: 3) Tat-ELP1-GFLG- (SEQ ID NO: 3) Dox (SEQ ID NO: 3) | 21.9 ± 8.2 | 1.1 ± 0.1 | 19.9 † |
| Tat-ELP2-GFLG-Dox (SEQ ID NO: 3) | 18.3 ± 11.4 | 17.3 ± 12.8 | 1.1 |

Table 1. IC$_{50}$ values for each construct. Data from FIG. 5 was fit to calculate the IC$_{50}$ value for each construct with treatment at 37° C. or 42° C. The thermal targeting index was calculated by dividing the IC$_{50}$ value for each construct at 37° C. by its IC$_{50}$ value with 42° C. treatment.
†, significant difference between the 37° C. and 42° C. IC$_{50}$ (p < 0.05, Student's t-test).
* IC$_{50}$ extrapolated from curve fitting because the required concentration was unreachable.

This calculation allows analysis of the enhancement of polypeptide toxicity by its hyperthermia induced phase transition. The IC$_{50}$ of free Dox was about 150 times lower than the Tat-ELP-GFLG (SEQ ID NO: 3) delivered Dox. The Dox IC$_{50}$ was enhanced by heat treatment, but the temperature enhancement was only 2.3 fold (p=0.02). Some toxicity was noted with the Tat-ELP1-GFLG (SEQ ID NO: 3) protein that does not contain Dox, especially when aggregation was induced with heat. However, the level of cell killing was ten-fold less potent than Tat-ELP1-GFLG-Dox (SEQ ID NO: 3). ELP1-GFLG-Dox (SEQ ID NO: 3), which is thermally responsive but lacks the Tat cell penetrating peptide, showed a slight thermal effect, but the potency was 2 fold higher at 37° C. and 15 fold higher at 42° C. than Tat-ELP1-GFLG (SEQ ID NO: 3). In fact, under hyperthermia conditions, Tat-ELP1-GFLG (SEQ ID NO: 3) is more toxic than ELP1-GFLG-Dox (SEQ ID NO: 3). Tat-ELP1-GFLG-Dox (SEQ ID NO: 3) was cytotoxic at 37° C., but relatively high concentrations were needed to achieve significant cell killing. However, the IC$_{50}$ was reduced 20 fold when Tat-ELP1-GFLG-Dox (SEQ ID NO: 3) treatment was combined with hyperthermia (p=0.04). The 20 fold enhancement of cytotoxicity induced by hyperthermia and Tat-ELP1-GFLG-Dox (SEQ ID NO: 3) treatment results from a combination of the toxicities of the Tat peptide and Dox. The Tat-ELP2-GFLG-Dox (SEQ ID NO: 3) IC$_{50}$ was unaffected by the hyperthermia treatment, indicating that the thermal enhancement of toxicity observed with the ELP 1-based construct was due to enhanced cellular delivery by aggregation of the polymer.

Figure 9:
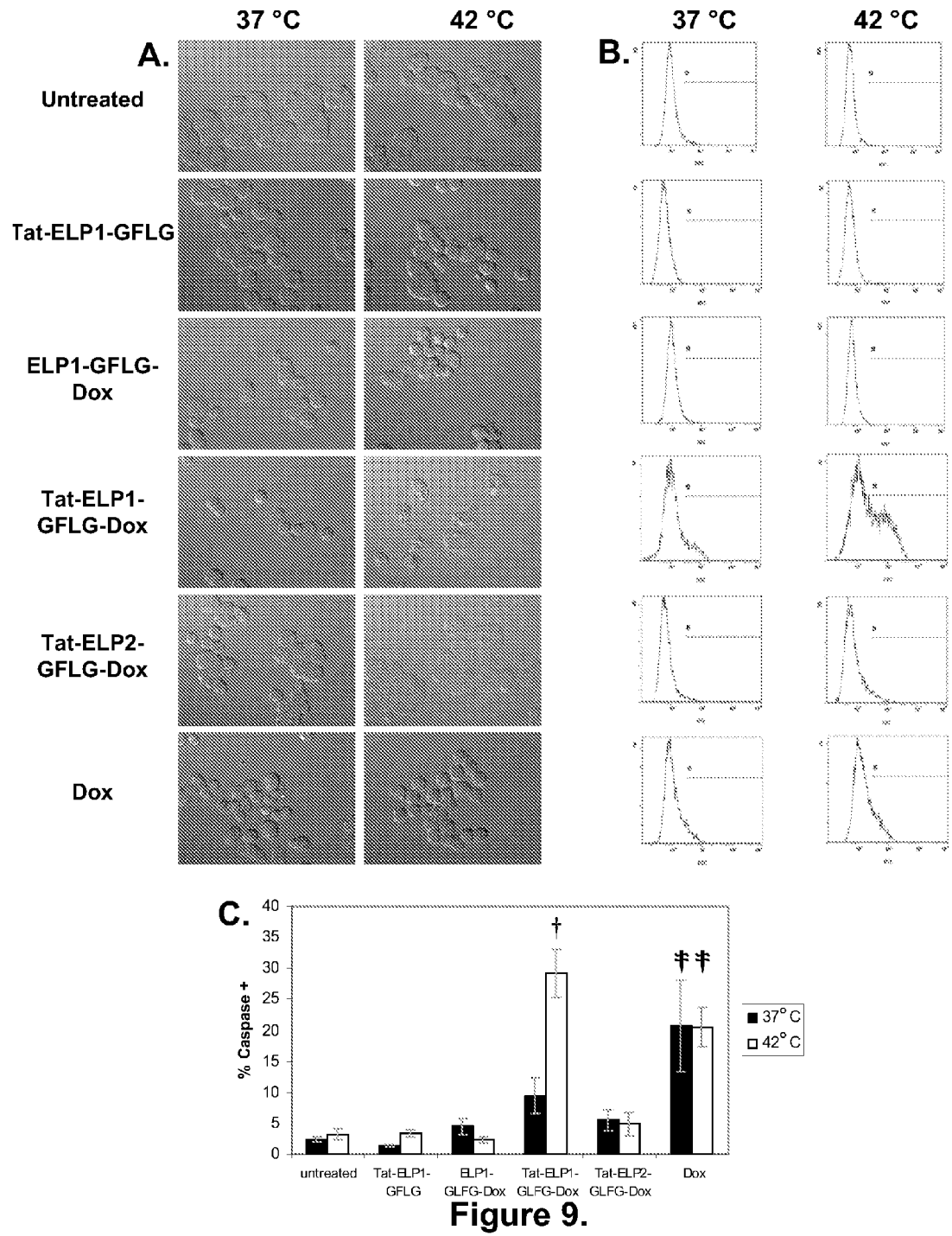
FIG. 9 shows induction of apoptosis by ELP-delivered Dox. DIC images of MES-SA cells were collected after treatment for 1 h with each construct (10 μM) at 37° C. or 42° C. (A). Histograms of caspase activation in MES-SA cells were obtained after the 1 h treatment (B). The percentage of cells with active caspases was measured from the histograms and averaged (C). Data represent the average of at least 3 experiments (bars, SEM). ‡, significant difference compared with untreated controls at 37° C. †, significant difference compared with Tat-ELP1-GFLG-Dox at 37° C. (p<0.0001, one was ANOVA, p<0.05, Scheffe's test). In the polypeptides identified in FIG. 9, GFLG is SEQ ID NO: 3.

2.6. Induction of Apoptosis. As mentioned above, hallmarks of apoptosis were noted in the cell morphology after treatment with Tat-ELP1-GFLG-Dox (SEQ ID NO: 3), especially in combination with hyperthermia. This effect was documented by treating MES-SA cells adhered to glass cover slips with each construct and imaging them by DIC microscopy. Cells were treated for 1 h as described above, then immediately mounted on slides and imaged without fixation. FIG. 9A shows representative images of each treatment population. Untreated cells were spread onto the glass, and morphological features such as nuclei and endocytic vesicles were readily visible. This morphology was not altered by simply exposing the cells to hyperthermia. When the cells were treated with Tat-ELP1-GFLG (SEQ ID NO: 3), their morphology was unaltered with treatment below the $T_t$, and treatment above the $T_t$ resulted in slight rounding and minor blebbing in only a small portion of the population. Cells treated with ELP1-GFLG-Dox (SEQ ID NO: 3) showed some hallmarks of apoptosis, including rounding and membrane blebbing. However, such effects were minor and limited to a fraction of the cells. Treatment with Tat-ELP1-GFLG-Dox (SEQ ID NO: 3) at 37° C. caused more extensive rounding and blebbing. When cells were treated with Tat-ELP1-GFLG-Dox (SEQ ID NO: 3) at 42° C., normal cell morphology was completely destroyed. All cells examined were rounded with no discernable nucleus and fragmented chromosomes. Tat-ELP2-GFLG-Dox (SEQ ID NO: 3) induced minor blebbing in a proportion of the population with no heat effect, similar to Tat-ELP1-GFLG-Dox (SEQ ID NO: 3) at 37° C. Free Dox also caused noticeable rounding and membrane blebbing, but not to the extent of Tat-ELP1-GFLG-Dox (SEQ ID NO: 3) at 42° C.

The mechanism by which Tat-ELP1-GFLG-Dox (SEQ ID NO: 3) induced apoptosis was investigated by determination of caspase activity. MES-SA cells were treated as described above, cells were harvested after the 1 h exposure, and caspase activity was detected using a fluorescent caspase inhibitor and flow cytometric analysis. A histogram of fluorescence versus cell number revealed two peaks, one with bright fluorescence which includes cells with positive caspase activity and one with lower fluorescence comprised of caspase negative cells (FIG. 9B). Cell numbers under each peak were quantified and averaged to determine the percentage of the cell population in which caspases were activated under each treatment condition. Caspase activity induced by hyperthermia alone, by Tat-ELP1-GFLG (SEQ ID NO: 3), or by ELP-GFLG-Dox (SEQ ID NO: 3) was similar to control levels (FIG. 9C). When cells were treated at 37° C., Tat-ELP1-GFLG-Dox (SEQ ID NO: 3) induced apoptosis slightly above control levels. However, when the treatment temperature was raised to 42° C., Tat-ELP1-GFLG-Dox (SEQ ID NO: 3) induced caspase activation in a significantly higher proportion of the population. In fact, the percent of caspase positive cells was enhanced almost 4 fold when cells were treated with Tat-ELP1-GFLG-Dox (SEQ ID NO: 3) at 42° C. versus 37° C. (p<0.05). Apoptosis induction by Tat-ELP2-GFLG-Dox (SEQ ID NO: 3) was not enhanced by hyperthermia, supporting the hypothesis that the higher levels of apoptosis seen with Tat-ELP1-GFLG-Dox (SEQ ID NO: 3) and hyperthermia were due to accumulation of the polypeptide as a result of the ELP phase transition. Free Dox induced apoptosis under the conditions tested (p<0.05), but the levels were not affected by hyperthermia.

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

Unless otherwise indicated, all numbers expressing quantities, specifically amounts set forth when describing experimental testing, are to be understood as being modified in all instances by the term "about." Accordingly, unless indicated to the contrary, the numerical parameters set forth herein are approximations that may vary depending upon the desired properties sought to be determined by the present invention Throughout this application, and specifically, below, various references are mentioned. All references are incorporated herein by reference in their entirety and should be considered to be part of this application.

REFERENCES

Schwarze, S. R., Ho, A., Vocero-Akbani, A., and Dowdy, S. F. In vivo protein transduction: delivery of a biologically active protein into the mouse. Science, 1999; 285: 1569-72.

Issels, R. D. Regional hyperthermia combined with systemic chemotherapy of locally advanced sarcomas: preclinical aspects and clinical results. Recent Results Cancer Res, 1995; 138: 81-90.

Feyerabend, T., Steeves, R., Wiedemann, G. J., Richter, E., and Robins, H. I. Rationale and clinical status of local hyperthermia, radiation, and chemotherapy in locally advanced malignancies. Anticancer Res, 1997; 17: 2895-7.

van Vulpen, M., Raaymakers, B. W., de Leeuw, A. A., van de Kamer, J. B., van Moorselaar, R. J., Hobbelink, M. G., Battermann, J. J., and Lagendijk, J. J. Prostate perfusion in patients with locally advanced prostate carcinoma treated with different hyperthermia techniques. J Urol, 2002; 168: 1597-602.

Falk, M. H. and Issels, R. D. Hyperthermia in oncology. Int J Hyperthermia, 2001; 17: 1-18.

Dewhirst, M. W., Prosnitz, L., Thrall, D., Prescott, D., Clegg, S., Charles, C., MacFall, J., Rosner, G., Samulski, T., Gillette, E., and LaRue, S. Hyperthermic treatment of malignant diseases: current status and a view toward the future. Semin. Oncol., 1997; 24: 616-25.

Takahashi, I., Emi, Y., Hasuda, S., Kakeji, Y., Maehara, Y., and Sugimachi, K. Clinical application of hyperthermia combined with anticancer drugs for the treatment of solid tumors. Surgery, 2002; 131: S78-84.

Meyer, D. E., Kong, G. A., Dewhirst, M. W., Zalutsky, M. R., and Chilkoti, A. Targeting a Genetically Engineered Elastin-like Polypeptide to Solid Tumors by Local Hyperthermia. Cancer Res, 2001; 61: 1548-54.

Dreher, M. R., Raucher, D., Balu, N., Michael Colvin, O., Ludeman, S. M., and Chilkoti, A. Evaluation of an elastin-like polypeptide-doxorubicin conjugate for cancer therapy. J Control Release, 2003; 91: 31-43.

Bidwell, G. L., 3rd and Raucher, D. Application of thermally responsive polypeptides directed against c-Myc transcriptional function for cancer therapy. Mol Cancer Ther, 2005; 4: 1076-85.

Massodi, I., Bidwell, G. L., 3rd, and Raucher, D. Evaluation of cell penetrating peptides fused to elastin-like polypeptide for drug delivery. J Control Release, 2005; 108: 396-408.

Maeda, H., Seymour, L. W., and Miyamoto, Y. Conjugates of anticancer agents and polymers: advantages of macromolecular therapeutics in vivo. Bioconjug. Chem., 1992; 3: 351-62.

Harker, W. G. and Sikic, B. I. Multidrug (pleiotropic) resistance in doxorubicin-selected variants of the human sarcoma cell line MES-SA. Cancer Res, 1985; 45: 4091-6.

Denny W A. DNA-intercalating ligands as anti-cancer drugs: prospects for future design. Anticancer Drug Des 1989; 4(4): 241-63.

Cassidy J, Duncan R, Morrison G J, Strohalm J, Plocova D, Kopecek J et al. Activity of N-(2-hydroxypropyl)methacrylamide copolymers containing daunomycin against a rat tumour model. Biochem Pharmacol 1989; 38(6): 875-879.

Maeda H, Seymour L W and Miyamoto Y. Conjugates of anticancer agents and polymers: advantages of macromolecular therapeutics in vivo. Bioconjug Chem 1992; 3(5): 351-362.

Takakura Y, Fujita T, Hashida M and Sezaki H. Disposition characteristics of macromolecules in tumor-bearing mice. Pharm Res 1990; 7(4): 339-346.

Yamaoka T, Tabata Y and Ikada Y. Distribution and tissue uptake of poly(ethylene glycol) with different molecular weights after intravenous administration to mice. J Pharm Sci 1994; 83(4): 601-606.

Duncan R, Coatsworth J K and Burtles S. Preclinical toxicology of a novel polymeric antitumour agent: HPMA copolymer-doxorubicin (PK1). Hum Exp Toxicol 1998; 17(2): 93-104.

Seymour L W, Duncan R, Kopeckova P and Kopecek J. Daunomycin- and adriamycin-N-(2-hydroxypropyl)methacrylamide copolymer conjugates; toxicity reduction by improved drug-delivery. Cancer Treat Rev 1987; 14(3-4): 319-327.

Yeung T K, Hopewell J W, Simmonds R H, Seymour L W, Duncan R, Bellini O., et al. Reduced cardiotoxicity of doxorubicin given in the form of N-(2-hydroxypropyl) methacrylamide conjugates: and experimental study in the rat. Cancer Chemother Pharmacol 1991; 29(2): 105-111.

St'astny M, Strohalm J, Plocova D, Ulbrich K and Rihova B. A possibility to overcome P-glycoprotein (PGP)-mediated multidrug resistance by antibody-targeted drugs conjugated to N-(2-hydroxypropyl)methacrylamide (HPMA) copolymer carrier. Eur J Cancer 1999; 35(3): 459-466.

Ryser H J and Shen W C. Conjugation of methotrexate to poly(L-lysine) increases drug transport and overcomes drug resistance in cultured cells. Proc Natl Acad Sci USA 1978; 75(8): 3867-3870.

Ohkawa K, Hatano T, Yamada K, Joh K, Takada K, Tsukada Y, et al. Bovine serum albumin-doxorubicin conjugate overcomes multidrug resistance in a rat hepatoma. Cancer Res 1993; 53(18): 4238-4242.

Minko T, Kopeckova P, Pozharov V and Kopecek J. HPMA copolymer bound adriamycin overcomes MDR1 gene encoded resistance in a human ovarian carcinoma cell line. J Control Release 1998; 54(2): 223-33.

Kopecek J, Kopeckova P, Minko T and Lu Z. HPMA copolymer-anticancer drug conjugates: design, activity, and mechanism of action. Eur J Pharm Biopharm 2000; 50(1): 61-81.

Kopecek J. Smart and genetically engineered biomaterials and drug delivery systems. Eur J Pharm Sci 2003; 20(1): 1-16.

Urry D W, Luan C-H, Parker T M, Gowda D C, Prasad K U, Reid M C et al. Temperature of Polypeptide Inverse Temperature Transition Depends on Mean Residue Hydrophobicity. J Am Chem Soc 1991; 113: 4346-4348.

Urry D W. Free energy transduction in polypeptides and proteins based on inverse temperature transitions. Prog Biophys Mol Bio 1992; 57(1): 23-57.

Meyer D E, Kong G A, Dewhirst M W, Zalutsky M R and Chilkoti A. Targeting a genetically engineered elastin-like polypeptide to solid tumors by local hyperthermia. Cancer Res 2001; 61(4): 1548-54.

Fujiwara K and Watanabe T. Effects of hyperthermia, radiotherapy and thermoradiotherapy on tumor microvascular permeability. Acta Pathol Jpn 1990; 40(2): 79-84.

Gerlowski L E and Jain R K. Effect of hyperthermia on microvascular permeability to macromolecules in normal and tumor tissues. Int J Microcirc Clin Exp 1985; 4(4): 363-72.

Jain R K. Transport of molecules across tumor vasculature. Cancer Metastasis Rev 1987; 6(4): 559-93.

Dreher M R, Raucher D, Balu N, Michael Colvin O, Ludeman S M and Chilkoti A. Evaluation of an elastin-like polypeptide-doxorubicin conjugate for cancer therapy. J Control Release 2003; 91(1-2): 31-43.

Vives E, Brodin P and Lebleu B. A truncated HIV-1 Tat protein basic domain rapidly translocates through the plasma membrane and accumulates in the cell nucleus. J Biol Chem 1997; 272(25): 16010-7.

Massodi I, Bidwell G L, 3rd and Raucher D. Evaluation of cell penetrating peptides fused to elastin-like polypeptide for drug delivery. J Control Release 2005; 108(2-3): 396-408.

Duncan R, Cable H C, Lloyd J B, Rejmanova P and Kopecek J. Degradation of side-chains of N-(2-hydroxypropyl) methacrylamide copolymers by lysosomal thiol-proteinases. Biosci Rep 1982; 2(12): 1041-6.

Bidwell G L, 3rd and Raucher D. Application of thermally responsive polypeptides directed against c-Myc transcriptional function for cancer therapy. Mol Cancer Ther 2005; 4(7): 1076-85.

Daniell H, Guda C, McPherson D T, Zhang X, Xu J and Urry D W. Hyperexpression of a synthetic protein-based polymer gene. Methods Mol Biol 1997; 63: 359-71.

Dewhirst M W, Prosnitz L, Thrall D, Prescott D, Clegg S, Charles C, et al. Hyperthermic treatment of malignant diseases: current status and a view toward the future. Semin Oncol 1997; 24(6): 616-25.

Meyer D E and Chilkoti A. Genetically encoded synthesis of protein-based polymers with precisely specified molecular weight and sequence by recursive directional ligation: examples from the elastin-like polypeptide system. Biomacromolecules 2002; 3(2): 357-67.

Minko T, Kopeckova P and Kopecek J. Comparison of the anticancer effect of free and HPMA copolymer-bound adriamycin in human ovarian carcinoma cells. Pharm Res 1999; 16(7): 986-96.

Demoy M, Minko T, Kopeckova P and Kopecek J. Time- and concentration-dependent apoptosis and necrosis induced by free and HPMA copolymer-bound doxorubicin in human ovarian carcinoma cells. J Control Release 2000; 69(1): 185-96.

Raucher D and Chilkoti A, Enhanced uptake of a thermally responsive polypeptide by tumor cells in response to its hyperthermia-mediated phase transition. Cancer Res 2001; 61(19): 7163-70.

Hovorka O, St'astny M, Etrych T, Subr V, Strohalm J, Ulbrich K et al. Differences in the intracellular fate of free and polymer-bound doxorubicin. J Control Release 2002; 80(1-3): 101-17.

Putnam D and Kopecek J. Polymer conjugates with anticancer activity. In: Adv Polym Sci, 1995. Vol. 122, pp. 55-123.

Minko T, Kopeckova P and Kopecek J. Efficacy of the chemotherapeutic action of HPMA copolymer-bound doxorubicin in a solid tumor model of ovarian carcinoma. Int J Cancer 2000; 86(1): 108-17.

Minko T, Kopeckova P and Kopecek J. Preliminary evaluation of caspases-dependent apoptosis signaling pathways of free and HPMA copolymer-bound doxorubicin in human ovarian carcinoma cells. J Control Release 2001; 71(3): 227-37.

Duncan R, Vicent M J, Greco F and Nicholson R I. Polymer-drug conjugates: towards a novel approach for the treatment of endrocine-related cancer. Endocr Relat Cancer 2005; 12 Suppl 1: S189-99.

Kaneko T, Willner D, Monkovic I, Knipe J O, Braslawsky G R, Greenfield R S and Vyas D M. New hydrazone derivatives of adriamycin and their immunoconjugates—a correlation between acid stability and cytotoxicity. Bioconjug Chem 1991; 2(3): 133-41.

Choksakulnimitr S, Masuda S, Tokuda H, Takakura Y and Hashida M. In vitro cytotoxicity of macromolecules in different cell culture systems. J Control Release 1995; 34(3): 233-41.

We claim:

1. A composition, comprising an ELP-containing protein, a GFLG (SEQ ID NO: 3) linker coupled thereto, and a therapeutic agent coupled with the linker, wherein the GFLG (SEQ ID NO: 3) linker comprises a C-terminal cysteine residue coupled to the therapeutic agent.

2. The composition of claim 1, wherein ELP is a five amino acid repeat comprising the sequence XGVPG (SEQ ID NO: 1), wherein X is any amino acid except proline.

3. The composition of claim 1, wherein the therapeutic agent is a chemotherapeutic agent.

4. The composition of claim 3, wherein the chemotherapeutic agent is doxorubicin.

5. The composition of claim 3, wherein the chemotherapeutic agent is methotrexate, vinblastin, or paclitaxel.

6. The composition of claim 1, comprising a cell-penetrating peptide sequence coupled with the ELP.

7. The composition of claim 6, wherein the cell-penetrating peptide sequence is a Tat peptide.

8. The composition of claim 6, wherein the cell-penetrating peptide is selected from Antp, Tat, MTS, Bac-7, Trans, and pVEC.

9. The composition of claim 1, which is Tat-ELP-GFLGC (SEQ ID NO: 4)—therapeutic agent.

10. The composition of claim 9, wherein the therapeutic agent is Dox.

11. The composition of claim 1, with a phase transition of about 39° C. to about 42° C.

12. A method of delivering a therapeutic agent to a tumor, comprising the steps of: administering a composition of claim 1; and applying local hyperthermia to the tumor site.

13. A method of treating, preventing, or managing cancer, comprising: administering a composition of claim 1; and applying local hyperthermia to a tumor site.

14. The method of claim 12 or claim 13, wherein the tumor is a breast tumor, lung tumor, colon cancer, or melanoma.

* * * * *